United States Patent [19]

Karimian et al.

[11] Patent Number: 5,677,302
[45] Date of Patent: Oct. 14, 1997

[54] THIADIAZOLE COMPOUNDS USEFUL AS PROTON PUMP INHIBITORS

[75] Inventors: Khashayar Karimian, Mississauga; Tim F. Tam, Woodbridge; Denis Desilets, Mississauga, all of Canada; Sue Lee, Randolph, N.J.; Tullio Cappelletto, North York, Canada; Wanren Li, Etobicoke, Canada

[73] Assignee: Apotex Inc., Weston, Canada

[21] Appl. No.: 606,987

[22] Filed: Feb. 26, 1996

[51] Int. Cl.$^6$ ............ C07D 513/06; A61K 31/535; A61K 31/495; A61K 31/415
[52] U.S. Cl. ............ 514/233.2; 548/128; 544/368; 544/134; 546/268.7; 514/338; 514/254; 514/361
[58] Field of Search ............ 548/128; 544/368, 544/134; 546/268.7; 514/338, 254, 233.2, 361

[56] References Cited

U.S. PATENT DOCUMENTS 3,864,353  2/1975  Haugwitz et al. .......... 260/306.8
5,225,414  7/1993  Henning et al. ............ 514/258

OTHER PUBLICATIONS

"The Chemistry of o-phenylene Di-isothiocyanate", Part 3, Griffiths et al., J.C.S. Perkin I, 2608–2611 (1980).
"The Chemistry of O-phenylene Di-isothiocyanate, Part 2 . . . ", Faull et al., pp. 2587–2590, J.C.S. Perkin I, 1980.
"The Thiadiazoles" William R. Sherman, Abbott Laboratories, North Chicago, Illinois, pp. 542–619 of Heterocyclic Compounds, 1, (1961), Chapter 7.
"E64 [trans-epoxycuccinyl-L-leucylamido-4(guanidino)butane]. . . " Gour-Salin et al., Biotechnology Research, Montreal, Canada, Biochemistry J. 1994, 299, 389–391.
"Chemical Reactions of Omeprazole & Omeprazole Analogs"IV, Bramdstrom et al., Acta Chemica Sandinavica 43 (1989) 577–583.
"1,2,4–Thiadiazoles", Frederick Kurzer, Advances in Heterocyclic Chemistry, vol. 12, pp. 286–398 (1982).
"Umsetzung von Mercapto–N–heterocyclenmit Arylcyanaten", Journal f. prakt. Chemie. Band 320, Heft 4, 1978, 677–684 J.A. Barth, Leipzig, Martin et al.
"Spaltung von 1,2,4–thiadiazol–3–onen . . . ", Journal f. prakt. Chemie, Band 330, Heft 3, 1988 S 338–348, Veb J.A. Barth, Leipzig Tittlebach et al.

"Exchange, Elimination, and Ring Opening Reactions . . . " Chem. Soc. Perkin Trans 1, 1985, 1007–1011, Martin et al.
"Toxic Effects of a Fungicide, 5–Ethoxy–3–(Trichloromethyl) . . . " Dalvi & Howell, Bulletin of Environmental Contamination & Toxicology, vol. 17, No. 2, 1977.
"Imidazo[1,2–d]–1,2,4–thiadiazoles" Pentimalli, et al., Gazzette Chimica Italiana, 107, 1977, pp. 1–5.
"Inhibitors of the Adenovirus Type 2 Proteinase Based on Substrate–Like Tetrapeptide Nitriles", Cornish et al., 1995 Bioorganic & Medicinal Chemistry Letters vol. 5, No. 1, pp. 25–30.
"Potent Inactivation fo Cathepsins S and L by Peptidyl . . . " Biol. Chem. Hoope–Seyler, vol. 375, pp. 343–347 May 1994, Brömme, et al.
"Vinyl Sulfones as Mechanism–Based Cysteine Protease Inhibitors" Palmer et al., J. Med. Chem. 1995, 38, 3193–3196.
"Molecular Basis of the Action of Drugs and Toxic Substances" Proceedings International Symposium, San Francisco, CA, Apr. 23–26, 1987, Singer et al. (ed.), pp.173–184.
"Chemical Reactions of Omeprazole & Omeproazole Analgos". . . Brandstrom et al., Acta Chemica Scandinavica 43 (1989) 536–548.
Grundemann et al., Org. Magnet. Res., 12(2), 95–97 Feb. 1979.
Martin et al., J. Chem. Soc. Perkin Trans. I, (1985), 5, 1007–1013.

*Primary Examiner*—Johann Richter
*Assistant Examiner*—Laura R. Cross
*Attorney, Agent, or Firm*—Ridout & Maybee

[57] ABSTRACT

Novel thiadiazole compounds are provided, which are effective as proton pumps inhibitors, useful in treating peptic ulcers by inhibition of the proton pump enzyme $H^+/K^+$-ATPase. The compounds are 3-substituted 1,2,4-thiadiazolo [4,5-α]benzimidazole and 3-substituted imidazo[1,2-d]-1,2,4-thiadiazoles corresponding to the general formula:

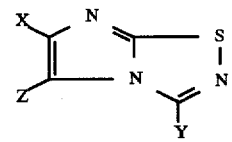

where X and Z either represent an optionally substituted benzene ring fused to the diazole nucleus, or represent a variety of independent chemical groupings (hydrogen, lower alkyl, halo, etc.) and Y is an electronegative group.

32 Claims, 4 Drawing Sheets

FORMULA I → RSH → FORMULA X

RSH → R-S-S-R +

FORMULA XI

FORMULA VIII   FORMULA XII

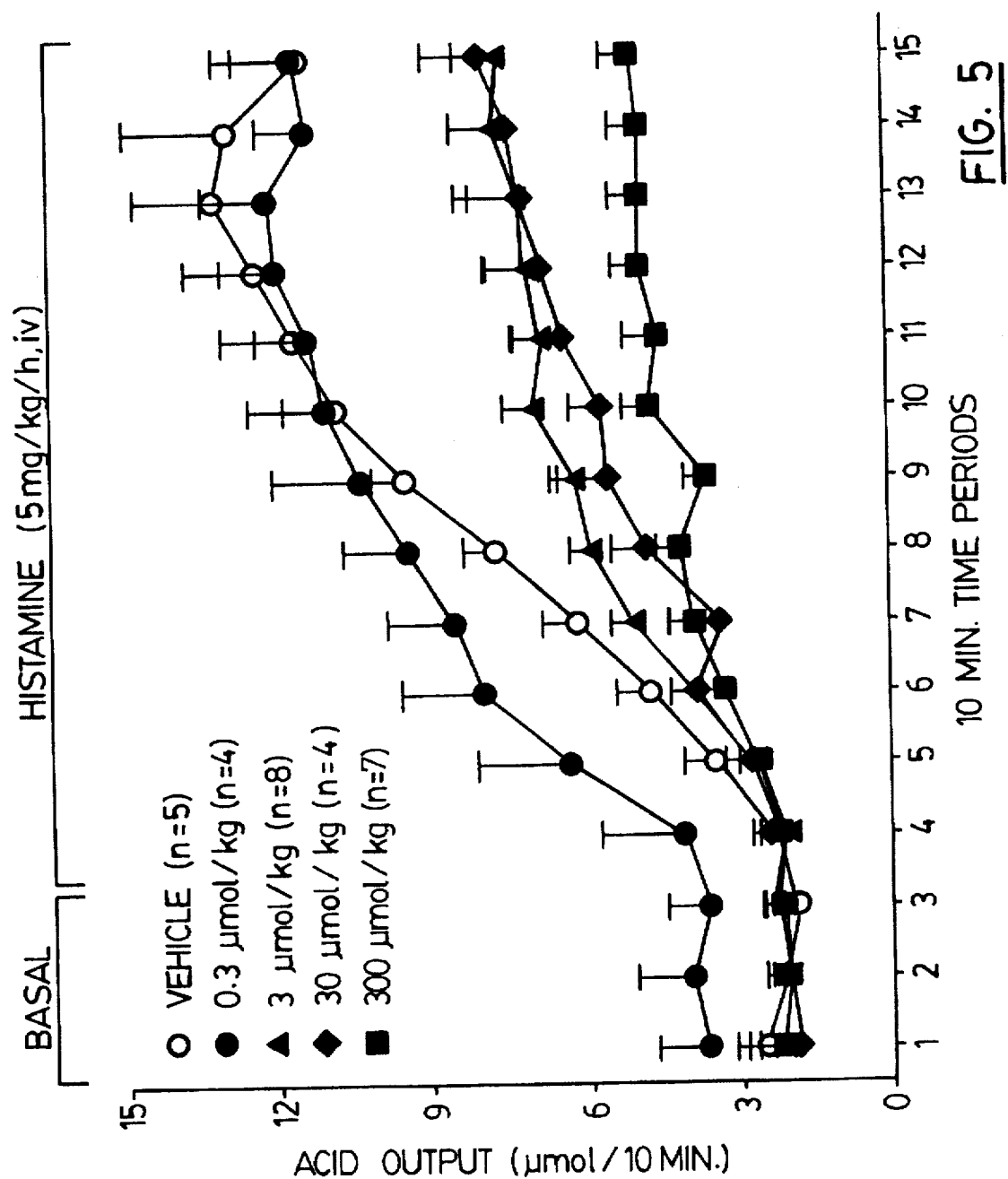

THIADIAZOLE COMPOUNDS USEFUL AS PROTON PUMP INHIBITORS

FIELD OF THE INVENTION

This invention relates to novel chemical compounds having pharmaceutical utility. More particularly, it relates to novel heterocyclic chemical compounds useful in the treatment of peptic ulcers in mammals, to methods for their synthesis and to compositions and uses thereof in peptic ulcer treatment in mammals.

BACKGROUND OF THE INVENTION AND PRIOR ART

Peptic ulcers are one of the most prevalent diseases in industrialized nations. Control of gastric acid secretion is the main therapy for peptic ulcers. Acid secretion is in turn brought about by the interaction of three physiological stimulants, gastrin, acetylcholine and histamine with their respective parietal cell receptors. Prior to the discovery of histamine $H_2$-receptor antagonists such as cimetidine and ranitidine, peptic ulcer treatment consisted of antacid therapy and anticholinergic drugs (eg. dicyclomine HCl). However, with the advent of $H_2$-receptor antagonists, treatment with anticholinergic agents has been largely supplanted by histamine $H_2$-receptor antagonist therapy. The development of this class of therapeutic entities presents one of the most important advances in the field of medicinal chemistry.

Another major development in the treatment of peptic ulcers has been realized with the introduction of $H^+/K^+$-ATPase inhibitors e.g. omeprazole. The enzyme $H^+/K^+$-ATPase, which is also known as the proton pump, is located in the membrane of gastric parietal cells and is responsible for the transport of protons from blood to lumen, which in turn results in decreasing the pH of stomach contents which leads to aggravation of peptic ulcers.

Omeprazole itself is in fact a prodrug which under acidic conditions converts to the active drug, namely its corresponding sulfenamide. The mechanism of action of omeprazole is well-studied and is known to involve a nucleophilic attack of one (or two) thiol group(s) of the $H^+/K^+$-ATPase on the sulfur atom of the chemically active sulfenamide. The resulting chemical modification of the thiol group(s) of the enzyme (formation of a disulfide bond between the $H^+/K^+$-ATPase sulfur and the sulfur of the benzimidazole pyridinium salt) causes the observed inhibition of the proton pump. The complex cascade of molecular events that lead to the inhibition of the $H^+/K^+$-ATPase is shown in FIG. 1.

As shown in FIG. 1, the presence of acid is a prerequisite to the conversion of omeprazole to its chemically active sulfenamide. However, the resulting sulfenamide is a labile molecule which transforms further to a number of other compounds that are unreactive to nucleophilic attack by the $H^+/K^+$-ATPase thiol(s) and are therefore incapable of inhibiting the enzyme. These transformations are acid catalyzed. Accordingly, in a strict chemical sense, while acid is a prerequisite for the conversion of omeprazole to its active form, it also acts to its detriment. As a partial solution to this problem, omeprazole drug products are formulated to resist the acidic medium of the stomach by enteric coating. The coating is dissolved in the relatively neutral environment of the duodenum and omeprazole is absorbed into the blood stream which carries the prodrug to the proton pump. It should be emphasized however, that the conversion of the prodrug to the active enzyme inhibitor can only be achieved in acidic media which also results in substantial degradation of the active sulfenamide. In summary, the instability of omeprazole in acidic environments, which is a prerequisite to its activation into a proton pump inhibitor, is the major shortcoming of this drug.

Acid instability of omeprazole not only decreases the bioavailability of the drug, but also creates considerable difficulty in its formulation, adding to the cost of the final drug product.

These inherent problems are also observed in the large number of omeprazole analogues that have been synthesized to increase the acid stability of their corresponding sulfenamide. Two factors contribute to the instability of omeprazole in acidic media. First, as observed with other sulfoxides, omeprazole undergoes a characteristic acid catalyzed degradation known as the Pummerer rearrangement. Second, protonation of the trivalent nitrogen of sulfenamide followed by nucleophilic attack on the sulfur atom is another characteristic reaction of these compounds. Enzyme inhibition is observed only when the $H^+/K^+$-ATPase-$S^-$ acts as the nucleophile. On the other hand, sulfenamide degradation is caused when $Cl^-$ acts as the nucleophile. Accordingly, any slight gain in acid stability of the sulfenamide (or sulfoxide) that may be introduced by chemical modification (resistance to $Cl^-$ attack) is offset by a decrease in reactivity of the analogue to $H^+/K^+$-ATPase-$S^-$ attack. The net result is a less effective drug.

Another shortcoming of omeprazole is its variability of action in different patients. There is clinical evidence of a variable response to omeprazole as determined by inhibition of gastric acid release in peptic ulcer patients, attributable to a high first pass effect for the biotransformation of omeprazole, and the fact that the metabolism of omeprazole appears to be under polymorphic genetic control, resulting in variable amounts of drug reaching the systemic circulation following a given dose.

SUMMARY OF THE INVENTION

It is an object of the present invention to provide novel pharmaceutical compounds, and compositions containing them, which are active as $H^+/K^+$-ATPase inhibitors, and hence useful in the treatment of peptic ulcers in mammals.

It is a further object of the invention to provide methods for the synthesis of such compounds.

The present invention is based upon the discovery of a class of new chemical compounds that are effective as $H^+/K^+$-ATPase inhibitors and are also acid stable. The new chemical compounds of the invention are characterized by an imidazo[1,2-d]-thiadiazole nucleus, with different substituents attached to the 3-position of the thiadiazolo heterocyclic ring structure.

Thus according to one aspect of the present invention, there are provided various 3-substituted 1,2,4-thiadiazolo[4,5-a]benzimidazole compounds and imidazo[1,2-d]-1,2,4-thiadiazole compounds corresponding to the general formula I:

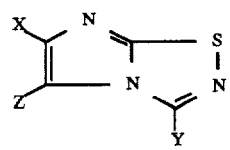

The groups represented by X and Z can be chosen from a wide variety of independent chemical groupings (hydrogen, lower alkyl, halo, nitro, amino, hydroxy, lower alkoxy, lower alkylamino, lower dialkylamino, etc) as more fully described hereinafter, to provide imidazo[1,2-d]-1,2,4-thiadiazoles. Alternatively, X and Z taken together can represent a benzene ring fused to the imidazo ring to form 1,2,4-thiadiazolo[4,5-a]benzimidazole compounds, with the benzene ring thereof being optionally substituted with up to four substituents independently selected from a wide variety of chemical groupings (hydrogen, lower alkyl, halo, nitro, amino, hydroxy, lower alkoxy, lower alkylamino, lower dialkylamino, etc).

The group Y at the 3-position of the thiadiazole nucleus is generally an electron withdrawing group, and can be any of the following groups:

(1) groups of the formula:

$$-\underset{R^7}{\overset{|}{C}}=O$$

in which $R^7$ represents hydrogen, hydroxy, lower alkyl, lower cycloalkyl, lower alkoxy, lower alkenyl, lower alkynyl, aryl, lower arylalkyl, heterocyclyl, heterocyclyloxy, heterocyclyl-loweralkylene, a group NR'R" where R' and R" are independently selected from hydrogen, lower alkyl, aryl and lower arylalkyl, or R' and R" when taken together form with the N-atom a five or six membered heterocyclic ring $$N\underset{\underline{\qquad}}{\overset{\frown}{\qquad}}(CH_2)_n$$

wherein n=4 or 5; and a group ANR'R", AOR' wherein A is an amino acid residue or a peptide of 2 to 3 amino acid residues and R', R" have the same definition as above (2) heterocyclyl, the heterocyclic ring being attached at any heteroatom or carbon atom which results in the creation of a stable structure, and the heterocyclic ring being optionally substituted with lower alkyl, lower acyl, lower alkoxycarbonyl, lower alkylsulfonyl or amido, with the proviso that the heterocyclyl is not 1-imidazolyl or substituted 1-imidazolyl;

(3) NR'R" wherein R', R" have the same definition as above (4) ANR'R", AOR' wherein A is an amino acid residue or a peptide of 2 to 3 amino acid residues and R', R" have the same definition as above (5) lower 2-(alkoxycarbonyl)alkyl (6) halo (7) groups of formula $R^8$-CHOH— wherein $R^8$ is hydrogen, lower alkyl, aryl, lower arylalkyl, lower cycloalkyl, lower alkenyl, lower alkynyl or heterocyclyl, the heterocyclic ring being attached at any heteroatom or carbon atom which results in the creation of a stable structure, (8) groups of formula $R^9$—C(=NOR$^{10}$)— wherein $R^{10}$ is hydrogen, lower alkyl or lower arylalkyl, and $R^9$ is lower alkyl, aryl, lower arylalkyl, lower cycloalkyl, lower alkenyl, lower alkynyl or heterocyclyl, the heterocyclic ring being attached at any carbon atom which results in the creation of a stable structure;

(9) lower alkoxy, lower arylalkoxy, lower cycloalkoxy, lower heterocyclylalkoxy or heterocyclyloxy;

(10) lower alkylsulfonyl, lower alkylsulfinyl, arylsulfonyl, arylsulfinyl, lower arylalkylsulfonyl, lower arylalkylsulfinyl, heterocyclylsulfonyl, heterocyclylsulfinyl; optionally substituted with 1 to 2 substituents selected from lower alkyl, halo, nitro, hydroxy, lower alkoxy, or groups of formula NR'R", OC(O)R', OC(O)OR', OC(O)NR'R", NR'(COR'), NHC(O)NR'R", NHC(O)OR' where R' and R" have the meanings given above;

(11) groups of the formula —C(=NOH)COOR$^{11}$ wherein $R^{11}$ is lower alkyl;

(12) lower alkyl, aryl, lower arylalkyl, lower cycloalkyl, each group being optionally substituted with 1 to 2 substituents selected from halo, nitro, amino, hydroxy, lower alkoxy, lower alkylamino, lower dialkylamino, NR'R", OC(O)R', OC(O)OR', OC(O)NR'R", NR' (COR'), NHC(O)NR'R", NHC(O)OR', with R' and R" having the meanings given above.

BRIEF REFERENCE TO THE DRAWINGS

FIG. 5 is a graphical presentation of the results of Example 40 below.

DESCRIPTION OF THE PREFERRED EMBODIMENTS

One class of preferred compounds according to the invention are 1,2,4-thiadiazolo[4,5-a]benzimidazoles corresponding to the following formula II:

(II)

or pharmaceutically acceptable salts thereof, wherein:

$R^1$, $R^2$, $R^3$, $R^4$ are independently hydrogen, lower alkyl, halo, nitro, amino, hydroxy, lower alkoxy, lower alkylamino, lower dialkylamino, NR'R", OC(O)R', OC(O)OR', OC(O)NR'R", NR'(COR'), NHC(O)NR'R", NHC(O)OR'.

R', R" are independently hydrogen, lower alkyl, aryl, lower arylalkyl or R' and R" in NR'R" when taken together with the N-atom, can form a five or six membered heterocyclic ring N (CH$_2$)$_n$ wherein n=4 or 5; and Y is as previously defined.

A second class of preferred compounds according to the present invention is imidazo[1,2-d]-1,2,4-thiadiazole of the following formula III:

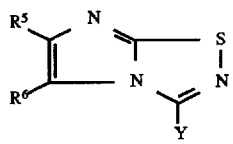

wherein $R^5$ and $R^6$ can have the same meanings as $R^1$, $R^2$, $R^3$ and $R^4$ in formula II above, and Y is as previously defined.

Figure 1:
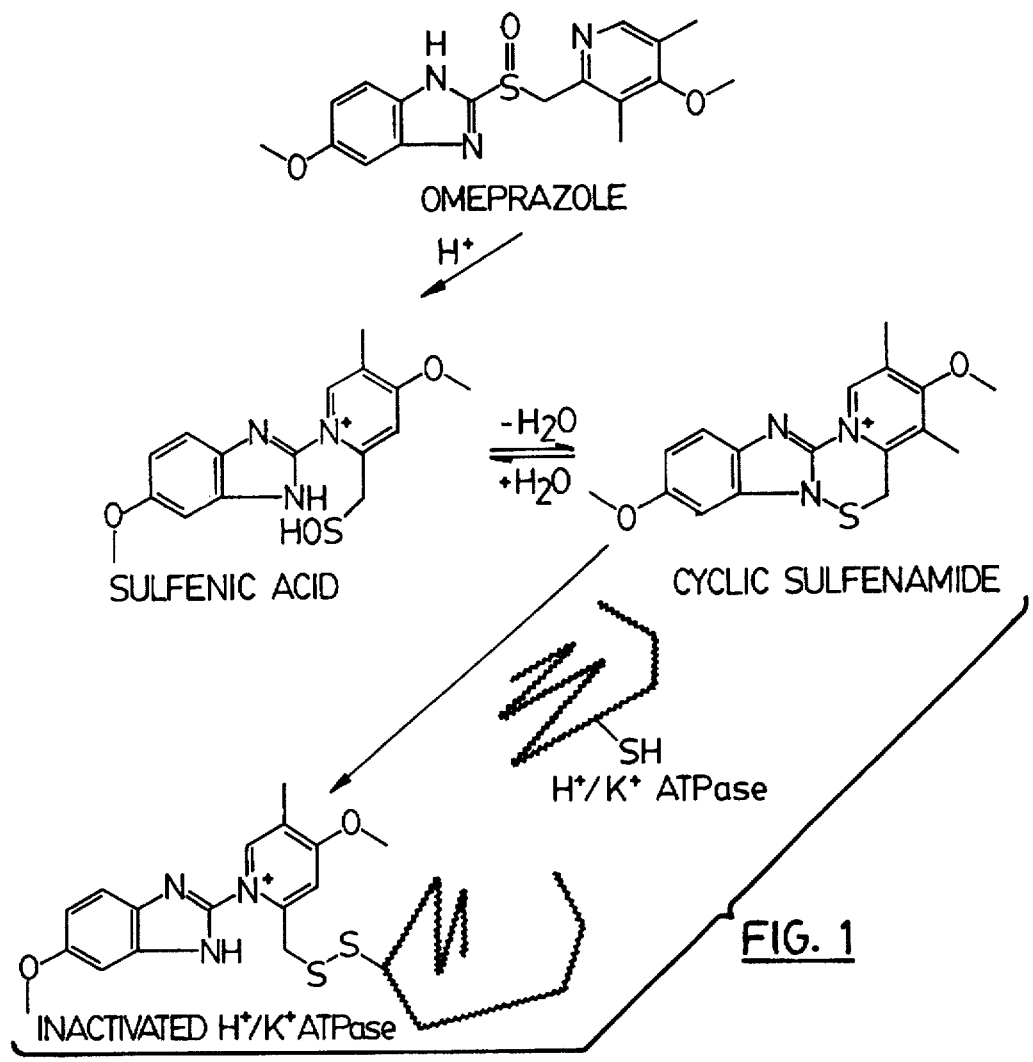
FIG. 1 is a diagrammatic representation of the mode of chemical interaction of omeprazole and H$^+$/K$^+$-ATPase.
Figure 2:
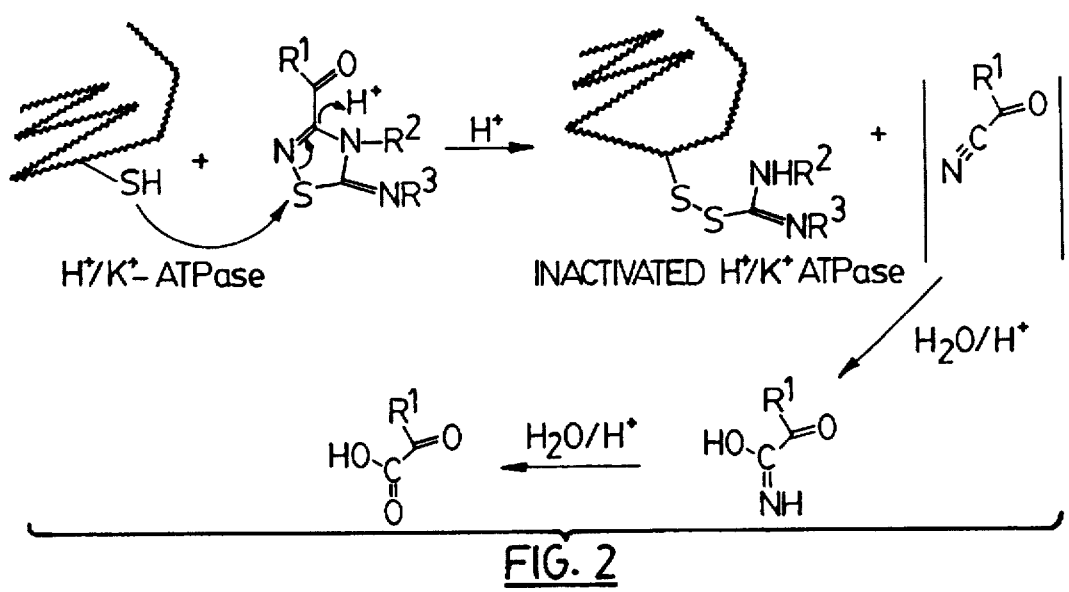
FIG. 2 is a similar diagrammatic representation of a proposed chemical interaction of compounds according to the invention with H$^+$/K$^+$-ATPase.

While it is not intended that the present invention should be limited to any particular theory or mode of action, it is believed that the compounds of the present invention interact to inhibit the action of the proton pump enzyme, by reacting with sulfhydryl groups on surface cysteine residues of the enzyme. This is generally illustrated in FIG. 2 of the accompanying drawings. The S—N bond in 1,2,4-thiadiazoles has a high energy content which originates, at least in part, from non-bonded electron repulsion between sulfur atom d orbitals and nitrogen atom p orbitals. 1,2,4-Thiazoles are therefore likely to be susceptible to nucleophilic attack. It has been reported over forty years ago that 1,2,4-thiadiazoles undergo S—N bond cleavage with reducing agents (Gordeler, Chem. Ber., 1954, 87, 57). The thiol groups of $H^+/K^+$-ATPase appear to act as reducing agents (nucleophiles), thereby become chemically modified as shown on FIG. 2, with resulting inhibition of the enzymatic activity. Group Y at the 3-position of the thiadiazole nucleus, because of its electron withdrawing nature, activates the adjacent bonds to facilitate this reaction.

Figure 3:
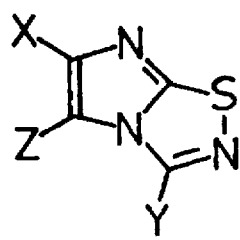
FIG. 3 shows the chemical reaction of a thiadiazolobenzimidazole compound with phenethylmercaptan.
Figure 3:
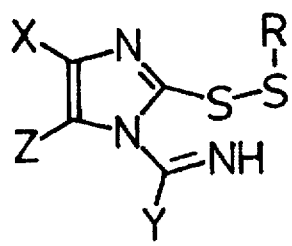
Figure 3:
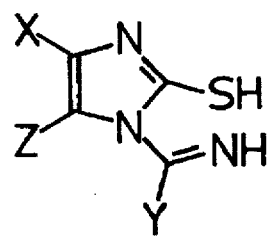
Figure 3:
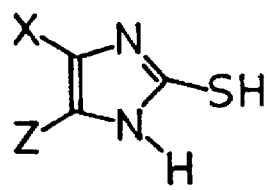
Figure 3:
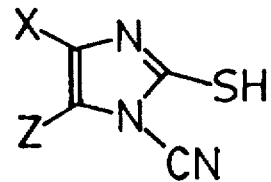

A useful in vitro model for obtaining an indication of the reactivity of thiadiazole compound towards the proton pump enzyme for deactivation thereof is provided by the reactivity of the thiadiazole compound towards phenethylmercaptan. The chemical mechanism of this process, as applied to the thiadiazolobenzimidazole compounds of the present invention, is diagrammatically illustrated on FIG. 3 of the accompanying drawings. The first stage of reaction forms a disulfide compound by cleavage of the S—N bond of the thiadiazole ring. This disulfide X cannot be isolated, since it reacts very rapidly with a second mercaptan group to give the disulfide of phenethylmercaptan and intermediate XI. In connection with the actual enzyme, the second step involving attack of another thiol group would not happen because of steric factors inhibiting the approach of two enzymes, or would lead to the formation of a disulfide bond in the event that another proximal thiol group is present. In both cases, this would lead to the inhibition of the enzyme. In some cases, intermediate XI further degrades to 2-mercaptobenzimidazole VIII or 1-cyano-2-mercaptobenzimidazole XII. A similar mechanism is followed by the imidazothiadiazoles of the present invention. Further description and discussion of this reaction and test method is included in the specific example section hereof.

Preferred compounds of formula II according to the invention are those in which $R^1$, $R^2$, $R^3$ and $R^4$ are each either hydrogen or lower alkoxy; and Y is (2-pyridyl)carbonyl or 2-pyridyl with the pyridyl ring in each case being optionally substituted with one to three substituents selected from methyl and methoxy, or lower alkoxy; Y is NR'R" where R' and R" are as previously defined, heterocyclyl (e.g. piperazino or morpholino), $R^7CO$ where $R^7$ is lower alkyl, aryl, hydroxy or hydrogen.

Particularly preferred compounds of formula II are those belonging to the following sub-classes:

(a) $R^1$, $R^3$ and $R^4$ are hydrogen, $R^2$ is lower alkoxy, and Y is (2-pyridyl)carbonyl wherein the pyridine ring is either unsubstituted or optionally substituted with 1-3 substituents selected from methyl and methoxy;

(b) $R^1$, $R^2$, $R^3$ and $R^4$ are each hydrogen, and Y is lower alkoxy, heterocyclyl especially nitrogen heterocyclyl, or $R^7CO$ wherein $R^7$ is alkyl, aryl, hydrogen or 2-pyridyl optionally substituted with up to 3 substituents selected from methyl and methoxy;

(c) $R^1$, $R^2$, $R^3$ and $R^4$ are each hydrogen, and Y is piperazino, morpholino, $R^7CO$ wherein $R^7$ is lower alkyl, phenyl or hydroxy.

The preferred compounds according to the present invention show specificity for the mercaptan functional group demonstrated by the fact that the imidazo[1,2-d]-thiadiazole nucleus of these compounds show limited or no reactivity towards other nucleophiles present in vivo such as amines, hydroxide or iodide ions. In chemical model systems, the heterocyclic ring of 1,2,4-thiadiazolo[4,5-a]benzimidazole in particular is unreactive towards these nucleophiles.

Particularly preferred compounds of formula III according to the invention are those in which $R^5$ and $R^6$ are hydrogen, and Y is $R^7CO$ wherein $R^7$ is lower alkyl, aryl, hydrogen, or 2-pyridyl optionally substituted with 1 to 3 substituents selected from methyl and methoxy.

As used herein:

The term "lower", as applied for example to lower alkyl, means 1 to 8 carbon atoms.

The term "aryl", alone or in combination, means a phenyl or naphthyl radical which optionally carries one or more substituents selected from alkyl, alkoxy, halogen, hydroxy, amino and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl and the like.

The term "arylalkoxy carbonyl", alone or in combination, means a radical of the formula —C(O)—O— arylalkyl, in which the term "arylalkyl" has the significance given below. An example of an arylalkoxycarbonyl radical is benzyloxycarbonyl.

The term "arylalkyl" means an alkyl radical in which one hydrogen atom is replaced by an aryl radical, such as benzyl, phenylethyl and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkylamino, such as 1,2,3,4-tetrahydro-2-naphthoyl, 2-acetamido-1,2,3,4-tetrahydro-2-naphthoyl.

The term "arylalkanoyl" means an acyl radical derived from an aryl-substituted alkanecarboxylic acid such as phenylacetyl, 3-phenylpropionyl, hydrocinnamoyl, 4-phenylbutyryl, (2-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acid, an optionally substituted benzoic or naphthoic acids such as benzoyl, 4-chlorobenzoyl, 4-carboxybenzoyl, 4-[(benzyloxy)carbonyl]benzoyl, 1-naphthoyl, 2-naphthoyl, 6-carboxy-2-naphthoyl, 6-[(benzyloxy) carbonyl]-2-naphthoyl,3-benzyloxy-2-naphthoyl, 3-hydroxy-2-naphthoyl, 3-[(benzyloxy) formamido]-2-naphthoyl, and the like.

The term "heterocyclyl", as used herein except where noted, represents a stable 5- to 7-membered mono or bicyclic or stable 7- to 10-membered bicyclic heterocyclic ring which is either saturated or unsaturated, and which consists of carbon atoms, and from one to three heteroatoms selected from the group consisting of N, O, S, and wherein the nitrogen and sulfur heteroatoms may be optionally oxidized, and the nitrogen atom may optionally be quaternized, and including any bicyclic group in which any of the above defined heterocyclic rings is fused to a benzene ring. The heterocyclic ring may be attached at any heteroatom or carbon atom which results in the creation of a stable structure. Examples of such heterocyclic elements, commonly known as heterocyclyl include piperidinyl, piperazinyl, 2-oxopiperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, furyl, tetrahydrofuryl, tetrahydropyranyl, thienyl, benzothienyl, tetrahydroquinolinyl (e.g. 1,2,3,4-tetrahydro-2-quinolinyl, etc.), 1,2,3,4-tetrahydroisoquinolinyl (e.g. 1,2,3,4-tetrahydro-1-oxo-isoquinolinyl etc.),quinoxalinyl, beta-carbolinyl, 2-benzofurancarbonyl, thiamorpholinyl, thiamorpholinyl sulfoxide, thiamorpholinyl sulfone, oxadiazolyl and the like. The heterocycle may be substituted in a manner which results in the creation of a stable structure.

"Amino acid residues" means any of the naturally occurring alpha-, beta-, and gamma-amino carboxylic acids, including their D and L optical isomers and racemic mixtures thereof, and the N-lower alkyl- and N-phenyl lower alkyl-derivatives of these amino acids. The amino acid residue is bonded through a nitrogen of the amino acid. The naturally occurring amino acids which can be incorporated into the present invention include, but are not limited to, alanine, arginine, asparagine, aspartic acid, cysteine, cystine, glutamic acid, glutamine, glycine, histidine, isoleucine, leucine, lysine, methionine, ornithine, phenylalanine, proline, serine, threonine, thyroxine, tryptophan, tyrosine, valine, beta-alanine, and gamma-aminobutyric acid. Preferred amino acid residues include proline, leucine, phenylalanine, isoleucine, alanine, γ-amino butyric acid, valine, glycine, and phenylglycine.

All alpha-amino acids except glycine contain at least one asymmetric carbon atom. As a result, they are optically active, existing in either D or L form as a racemic mixture. Accordingly, some of the compounds of the present invention may be prepared in optically active form, or as racemic mixtures of the compounds claimed herein.

The term "A" wherein A is an amino acid or peptide of 2 to 3 amino acid residues refers to an amino acid or a peptide diradical starting with the HN— radical on the left hand side of A and terminated by the —C(O) radical on the right hand side. For example, the amino acid glycine is abbreviated HAOH wherein A is HN—CH$_2$—C(O).

The term "aryloxyalkanoyl" means an acyl radical of the formula aryl-O-alkanoyl.

The term "heterocyclyloxycarbonyl" means an acyl group derived from heterocyclyl-O—CO— wherein heterocyclyl is defined above.

The term "heterocyclylalkanoyl" is an acyl radical derived from a heterocyclyl-substituted alkane carboxylic acid wherein heterocyclyl has the same significance given above.

The term "heterocyclylalkoxycarbonyl" means an acyl radical derived from a heterocyclyl-substituted alkyl-O—COOH wherein heterocyclyl has the same significance given above.

The term "aminoalkanoyl" means an acyl radical derived from an amino-substituted alkanecarboxylic acid wherein the amino group can be a primary, secondary or tertiary amino group containing substituents selected from hydrogen, and alkyl, aryl, arylalkyl, cycloalkyl, cycloalkylalkyl radicals and the like.

"Pharmaceutically acceptable, non-toxic salts" refers to pharmaceutically acceptable salts of the compounds of this invention which retain the biological activity of the parent compounds and are not biologically or otherwise undesirable (e.g. the salts are stable). Salts of the two types may be formed from the compounds of this invention: (1) salts of inorganic and organic bases from compounds of Formula I which have a carboxylic acid functional group. (2) Acid addition salts may be formed at the amine functional group of many of the compounds of this invention.

Pharmaceutically acceptable salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary and tertiary amines, substituted amines including naturally occurring substituted amines, cyclic amines and basic ion exchange resins. Such salts are exemplified by, for example, isopropopylamine, trimethylamine, diethylamine, triethylamine, tripropylamine, ethanolamine, 2-dimethylaminoethanol, tromethamine, dicyclohexamine, lysine, arginine, histidine, caffeine, procaine, hydrabramine, choline, betaine, ethylenediamine, glucosamine, metylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Pharmaceutically acceptable acid addition salts are formed with inorganic acids such as hydrochloric acid, hydrobromic acid, sulfuric acid, nitric acid, phosphoric acid and the like and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "animals" refers to humans as well as all other animal species, particularly mammals (e.g. dogs, cats, horses, cattle, pigs etc.), reptiles, fish, insects and helminths.

The specific, most preferred compounds according to the present invention are the following:

3-(1-oxoethyl)-1,2,4-thiadiazolo[4,5-a]benzimidazole, which has the following chemical formula:

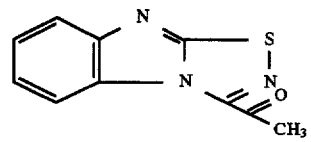

3-(1-oxophenylmethyl)-1,2,4-thiadiazolo[4,5-a] benzimidazole, which has the following chemical formula:

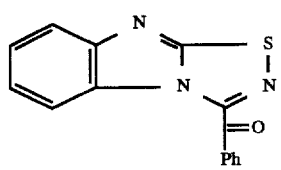

3-(2-pyridyl)-1,2,4-thiadiazolo[4,5-a]benzimidazole, which has the following chemical formula:

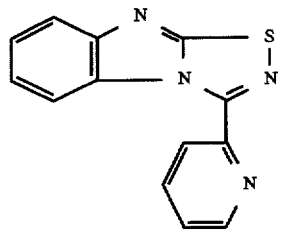

3-(4-methyl-1-piperazinyl)-1,2,4-thiadiazolo-[4,5-a]benzimidazole, which has the following chemical formula:

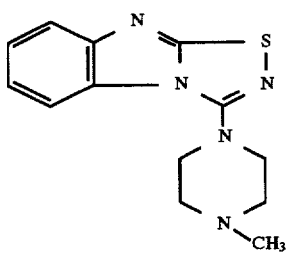

3-(4-morpholinyl)-1,2,4-thiadiazolo[4,5-a]benzimidazole, which has the following chemical formula:

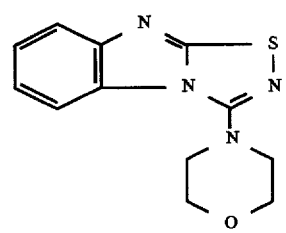

3-(1-pyrrolidinyl)-1,2,4-thiadiazolo[4,5-a]benzimidazole, which has the following chemical formula:

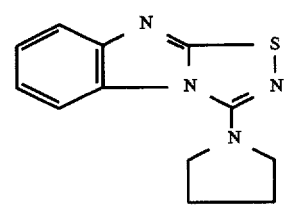

3-bromo-1,2,4-thiadiazolo[4,5-a]benzimidazole, which has the following chemical formula:

3-[(4-methoxy-3,5-dimethyl -2-pyridyl)oxomethyl]-1,2,4-thiadiazolo[4,5-a]benzimidazole, which has the following chemical formula:

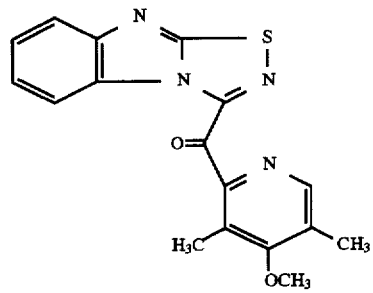

3-carboxy-1,2,4-thiadiazolo-[4,5-a]benzimidazole which has the following chemical formula:

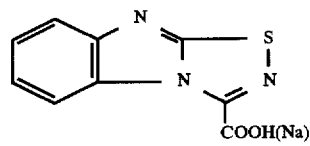

7-methoxy-3-[(4-methoxy-3,5-dimethyl -2-pyridyl)oxomethyl]-1,2,4-thiadiazolo[4,5-a]benzimidazole, which has the following chemical formula:

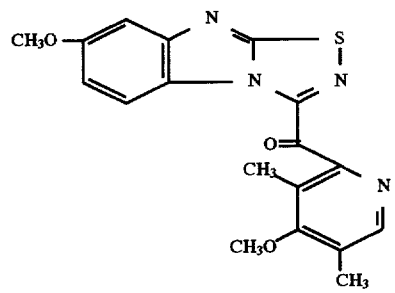

3-(4-methylphenylsulfonyl)-1,2,4-thiadiazolol[4,5-a]benzimidazole, which has the following chemical formula:

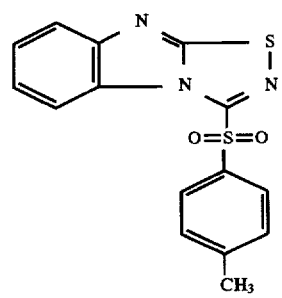

3-(1-oxoethyl)imidazo[1,2-d]-1,2,4-thiadiazole, which has the following chemical formula:

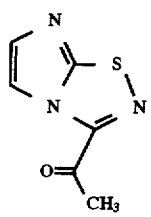

3-(oxophenylmethyl)imidazo[1,2-d]-1,2,4-thiadiazole, which has the following chemical formula:

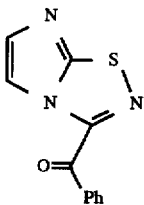

3-(4-acetyl-1-piperazinyl)-1,2,4-thiadiazolo[4,5-a]benzimidazole, which has the following chemical formula:

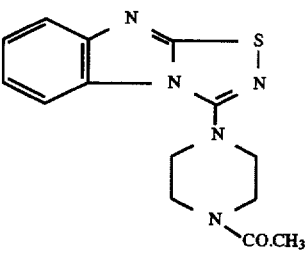

The present invention provides synthetic methods for preparing compounds according to the invention. Some of these methods involve conversion of one compound according to the invention into another, different such compound. The choice of method depends largely upon the desired Y group, i.e. the substituent on the 3-position in the final compound.

In a first process, the corresponding 3-oxo compound of formula IV, carrying a lower alkyl or lower arylalkyl substituent at position 2 is reacted with YCN in an inert solvent. This method is appropriate for compounds in which Y is lower alkyl, aryl, arylalkyl, cycloalkyl, 1-haloalkyl, 1,1-dihaloalkyl, heterocyclyl, lower alkylsulfonyl or arylsulfonyl. The reaction can be represented as follows:

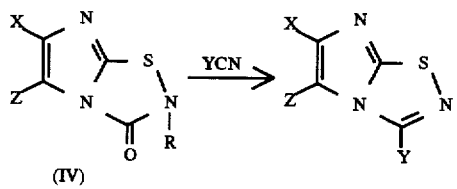

The appropriate nitrile compounds YCN wherein Y is lower alkyl, arylalkyl, cycloalkyl, 1-haloalkyl, 1,1-dihaloalkyl, or heterocyclyl are for the most part commercially available e.g. from Aldrich Chemical Co. Alternatively, they can be prepared by methods known in the Art (see for example Chapter 17 in Organic Functional Group Preparations, Vol. I by Sandler and Karo, Academic Press, 1983). Acetonitrile, benzonitrile, 2-cyanopyridine, cyclopentylcyanide, dibromoacetonitrile, 6-cyanopurine and p-toluenesulfonyl cyanide are some typical examples. The reaction normally takes place at elevated temperature between 70° to 140° C. in an inert solvent such as toluene, dimethylformamide for a period of 6 to 24 hours, preferably 16 hours. In some cases, YCN is used as the solvent. The product is isolated by conventional means.

Compounds of formula I in which Y is amino, lower alkylamino, lower dialkylamino, thioalkyl can also be prepared by using compounds of formula YCN wherein Y is amino, lower alkylamino, lower dialkylamino or lower thialkyl. Examples of YCN is this category are cyanamide, 1-piperidinecarbonitrile, methyl thiocyanate which are commercially available. Compounds YCN can also be synthesized from cyanogen bromide according to literature procedures (see p.174, Fieser and Fieser, Reagents in Organic Synthesis, John Wiley and Sons, 1967).

2-Alkyl-1,2,4-thiadiazolo[4,5-a]benzimidazole-3(2H)-ones of formula IV are prepared from alkyl isocyanate and 2-mercaptobenzimidazole according to the procedure of Martin et al., Tetrahedron, 1983, 39, 2311. 2-Alkylimidazo[1,2-d]-1,2,4-thiadiazole-3(2H)-ones of formula IV are prepared from alkyl isocyanate and 2-mercaptoimidazole according to the procedure of Tittlebach et al., J. Prakt Chem. 1988, 330, 338–348. The 2-mercaptobenzimidazoles are either commercially available, or can be prepared by methods well known in the art or readily available in the literature. Commercially available 2-mercaptobenzimidazoles includes 5-methyl-2-mercaptobenzimidazole, 5-methoxy-2-mercaptobenzimidazole, 5-chloro-2-mercaptobenzimidazole. Suitable 2-mercaptobenzimidazole which are not commercially available can be prepared by known methods. Preparative method include those of Billeter et al., Ber., 1887, 20, 231, Org. Synth., Coll. Vol. 4, 569, Futaki et al., J. Pharm. Soc. Jpn., 1954, 74, 1365, Bucknall et al., Nature, 19670 213, 1099.

In a second, similar process, applicable for the preparation of compounds in which group Y in the final compound is $R^7$—C=O and $R^7$ is lower alkyl, aryl, lower arylalkyl, lower cycloalkyl, lower alkoxy, amino, lower alkylamino, lower dialkylamino, heterocyclyl, the heterocyclic ring being attached at any heteroatom or carbon atom which results in the creation of a stable structure, NR'R", ANR'R", AOR' wherein A is an amino acid residue or a peptide of 2 to 3 amino acid residues and R', R" have the same definition as above, a compound of general formula

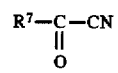

is reacted with the corresponding 3-oxo compound carrying a lower alkyl or lower arylalkyl substituent at position 2, i.e. a compound of formula IV used in process A above, thus:

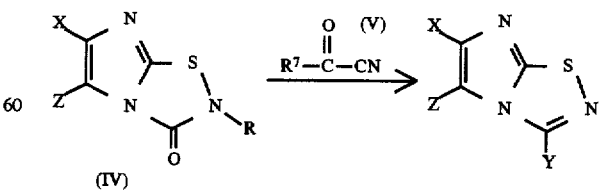

The reaction may be carried out in an inert solvent such as dichloromethane, tetrahydrofuran or dimethylformamide. The reaction takes place at room temperature over a period of 3 to 48 hours, usually about 6 hours. The resulting solid is then isolated by conventional means.

Most cyanoketones, cyanoester derivatives of formula V are commercially available. The cyanoketone derivatives used in this invention are either commercially available or can be prepared by methods known in the art. The commercially available cyanoketones include, benzoyl cyanide, acetyl cyanide, methoxycarbonyl cyanide. A list of commercially available cyanide derivatives is available (Chem Sources, U.S.A., 24th Ed., 1983, Directories Publishing Company Inc., Ormont Beach, Fla.). Appropriate cyanoketones, cyanoesters which are not commercially available can be readily prepared by methods known in the art such as the ones described in Mathieu et al., Formation of C—C Bonds, Vol I, p. 456–457, Georg Thieme Verlag, 1973, Stuttgart. Other suitable methods include those of Koenig et al., Tet. Lett., 1974, 2275 and Ando et al., Synthesis, 1983, 637. These methods include reacting an acid chloride with cuprous cyanide or potassium cyanide.

Alternatively, compounds of formula I in which Y is $R^7$—C=O wherein $R^7$ has the same definition as above can be prepared by the hydrolysis of compounds of formula I wherein Y is $R^7$—C(Hal)$_2$ and wherein Hal is a halogen, preferably chlorine, bromine or iodine. Such an hydrolysis can be carried out in a strongly acidic media or in aqueous silver nitrate, and can be represented thus:

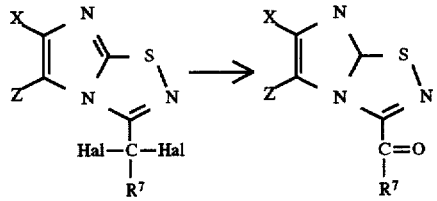

A third process for making the same end products as in the case of the second process described above, involves, as a final step, reacting a 2-thioether diazole compound of formula VI with m-chloroperbenzoic acid (MCPBA) in an inert solvent, to effect cyclization to form the 1,2,4-thiadiazole ring, and can be represented as follows:

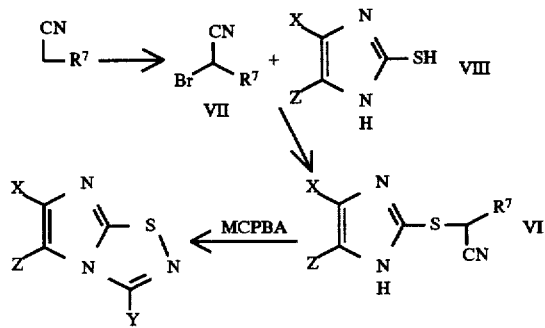

A bromoheterocyclylacetonitrile derivative (VII) can be reacted with 2-mercaptobenzimidazole (VIII) in base to give a compound of formula VI. Examples of those bases are sodium hydroxide or potassium hydroxide. The reaction takes place in a mixture of water and alcohol at room temperature for about 1 to 16 hours, preferably 8 hours, the product compound VI is isolated by conventional means.

Compound VI reacts with m-chloroperbenzoic acid, in an inert solvent such as dichloromethane, or 1,2-dichloroethane to give the compound of formula I where Y is $R^7$—C=O. The reaction takes place at room temperature for about 3 to 8 hours, preferably 3 hours. The product is isolated by conventional means.

The bromoheterocyclylacetonitrile (VII) derivative is in turn prepared by reacting a compound of formula IX with N-bromosuccinimide in an inert solvent such as carbon tetrachloride.

A fourth process uses a compound of formula I in which Y is $R^7$—C=O (formula IA) as the starting material, and derivatizes it to a compound of formula I in which Y is —CHOH—$R^7$ (formula IB) or —C=(NOR$^{10}$)—$R^7$ (formula IC), or —COOH (formula ID), thus:

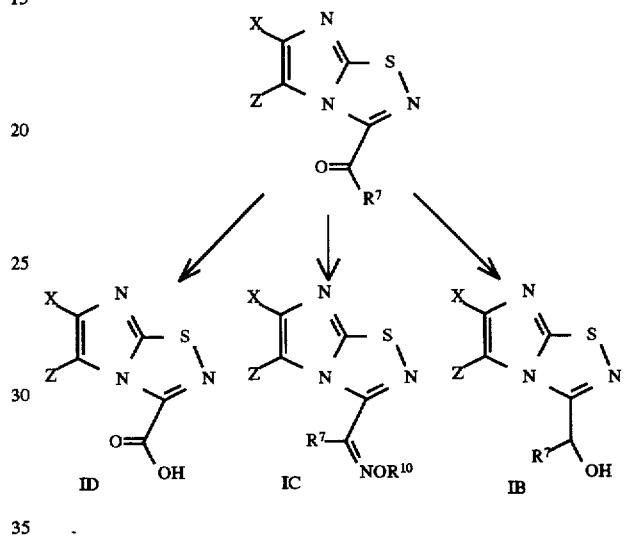

Compounds of formula IB can be prepared by the reduction of the corresponding compounds of formula IA wherein Y is $R^7$—C=O with sodium borohydride, or sodium cyanoborohydride in alcohol. Compound of formula IB is isolated by conventional means.

Compounds of formula IC can be prepared by reacting compound of formula I wherein Y is $R^7$—C=O with hydroxylamine derivatives. Examples of hydroxylamines are hydroxylamine, methoxylamine, ethoxylamine, benzyloxylamine. The conversion of a ketone to an oxime is well-documented in the art (see, for example, Sandler and Karo, Organic Functional Group Preparations, 1989, Vol. III, Chapter 11).

Compounds of formula ID in which $R^7$ is hydroxy can be prepared by the base hydrolysis of the compounds of formula I wherein Y is $R^7$—C=O and $R^7$ is lower alkoxy. The reaction is carried out in 1M sodium hydroxide at room temperature in a mixture of water and an organic solvent such as methanol, ethanol, 1,4-dioxane or acetonitrile. The product is isolated by conventional means after neutralization of the base with diluted acid.

A fifth process, applicable to the preparation of compounds of formula I according to the invention in which Y represents halogen, uses the same starting compound of formula IV as used in process A and process B, and reacts it with cyanogen halide, thus:

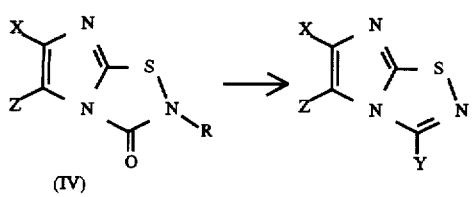

(IV)

The reaction takes place in an inert solvent. The compound is isolated by conventional means.

A sixth process uses as starting materials the compounds of formula I where Y represents halogen, compounds prepared according to process E above, and reacts them with a primary or secondary amine, or alcohol, to give a compound of formula I wherein Y is NR'R", AOR', ANR'R", OR'. R', R" have the same definition as above. This process proceeds best when Y in the starting material is bromine. It can be represented thus:

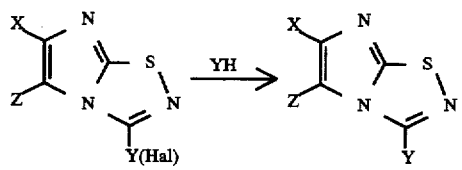

Nucleophiles such as lower alkoxides, aryloxides, lower arylalkoxides, lower cycloalkoxides, ammonia, lower alkylamines, lower dialkylamines, heterocyclic amines, HNR'R", HANR'R", HAOR'. wherein A is an amino acid residue or a peptide of 2 to 3 amino acid residues, react with compounds of formula I wherein Y=bromide in an inert solvent to give compounds of formula I wherein Y is lower alkoxy, aryloxy, lower arylalkoxy, lower cycloalkoxy, amino, lower alkylamino, lower dialkylamino, NR'R", ANR'R", AOR', wherein A is an amino acid residue or a peptide of 2 to 3 amino acid residues.

A seventh process uses as starting materials compounds of formula I according to the invention in which Y represents COOH (preparable by process D above), and reacts them with an amine to give a compound of formula I wherein Y is CO—$R^7$, wherein is NR'R", AOR', ANR'R", thus:

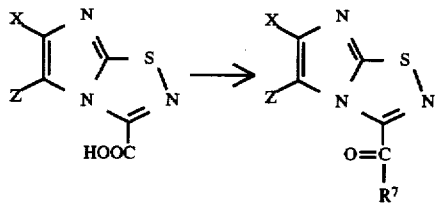

In this way, compounds of formula I in which Y is $R^7$—C=O and $R^7$ is NR'R", AOR', ANR'R" can be prepared by reacting the carboxylic acid compound of formula I wherein Y is COOH with an amino acid amide HANR'R", or amines HNR'R", or amino acid ester HAOR', in the presence of a dehydrating agent such as 1-(3-dimethylaminopropyl)-3-ethyl carbodiimide (EDCI) and hydroxybenzotriazole in an inert solvent such as tetrahydrofuran, dimethylformamide, dichloromethane.

An eighth process applicable to the preparation of compounds of Formula 1 in which Y represents lower alkylsalkylsulfonyl, arylsulfonyl, heterocyclylsulfonyl, lower arylalkylsulfonyl, lower alkylsulfinyl, arylsulfinyl, heterocyclylsulfinyl or lower arylalkylsulfinyl comprises the reaction of the corresponding thioether compound with the predetermined stoichiometric amount of an oxidizing agent, thus:

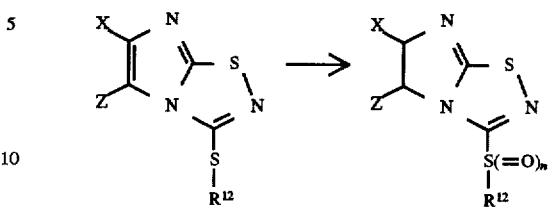

where n is 1 or 2 and $R^{12}$ represents lower alkyl, lower arylalkyl or aryl. A preferred oxidizing agent for use in this process is metachloroperbenzoic acid mCPBA, but there are many other, suitable such oxidizing agents.

A significant feature of the preferred compounds of this invention is that these compounds are heterocycles with molecular weight less than 450. Low molecular weight compounds are generally more bioavailable. The spectrum of log P of these molecules, i.e. the partition coefficient between octanol and water, varies from 0.5 to 4.0 which covers the lipophilicity range of most known drugs.

Figure 4:
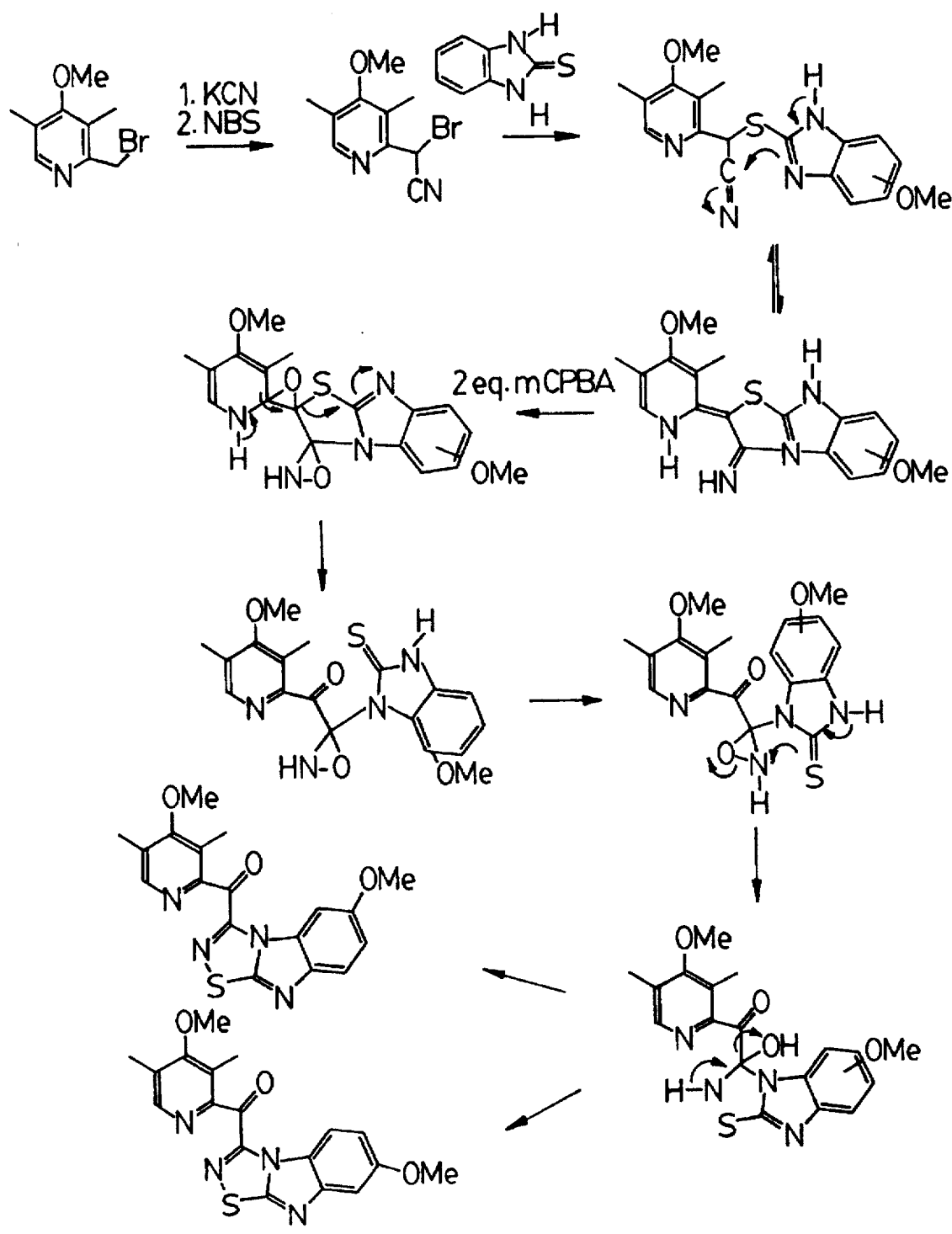
FIG. 4 is a graphical representation of a specific synthesis route for the most preferred compound according to the present invention.

The specific, most preferred compound according to the present invention is 7-methoxy-3-[(4-methoxy-3,5-dimethyl-2-pyridyl)oxomethyl]-1,2,4-thiadiazolo[4,5-a]benzimidazole. This molecule carries an electron-withdrawing group at the 3-position of the heterocyclic ring. It has limited solubility in water. A specific synthesis route for it, in accordance with the invention, is illustrated on FIG. 4 of the accompanying drawings. Its structure was proved by X-ray crystallography. $^1$H and $^{13}$C NMR, IR, mass spectrometry and elemental analysis provided additional evidence for the chemical identity of this compound. Further specific details of its preparation, characterization and properties are given in the specific examples below. It is active in the suppression of gastric acid secretion in animal model.

For the treatment of peptic ulcers, the compounds of the invention may be administered orally, topically, or parenterally in dosage unit formulations containing conventional non-toxic pharmaceutically acceptable carriers, adjuvants and vehicles. The term parenteral as used herein includes subcutaneous injection or infusion techniques. In addition to the treatment of warm-blooded animals such as mice, rats, horses, cattle, sheep, dogs, cats, etc., the compounds of the invention are effective in the treatment of humans.

For compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as liquid pharmaceutically administrable compositions can, for example, be prepared by dissolving, dispersing, etc. an active compound as defined above and optional pharmaceutically adjuvants in a carrier, such as, for example, water, saline, aqueous dextrose, glycerol, ethanol, and the like, to thereby form a solution or suspension. If desired, the pharmaceutical composition to be administered may also contain a minor amount of non-toxic auxiliary substances such as wetting or emulsifying agents and the like, for example, sodium acetate, sorbitan monolaurate, triethanolamine sodium acetate, triethanolamine oleate, etc. Actual methods of preparing such dosage forms are known, or will be apparent to those skilled in this art: for example, see Remington's Pharmaceutical Sciences, Mack Publishing Company, Easton, Pa., 15th Edition, 1975. The composition of formulation to be administered will, in any event, contain a quantity of the active compound(s) in an amount effective to alleviate the symptoms of the subject being treated.

The pharmaceutical compositions containing the active ingredient may be in a form suitable for oral use, for example, as tablets, troches, lozenges, aqueous or oily suspensions, dispersible powders or granules, emulsions, hard and soft capsules, or syrups or elixirs. Compositions intended for oral use may be prepared according to any method known to the art for the manufacture of pharmaceutical compositions and such compositions contain one or more agents from the group consisting of sweetening agents, flavouring agents, colouring agents and preserving agents in order to provide pharmaceutically elegant and palatable preparations. Tablets contain the active ingredient in admixture with the non-toxic pharmaceutically acceptable excipients which are suitable for the manufacture of tablets. The excipients may be for example, inert diluents, such as calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be coated by known techniques to delay the disintegration and absorption in the gastrointestinal tract and thereby provide a sustained action over a long period. For monostearate or glyceryl distearate may be employed.

Formulations for oral use may also be presented as hard gelatin capsules wherein the active ingredients are mixed with an inert solid diluent, for example, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with the excipient suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum and gum acacia; dispersing or wetting agents may be a naturally-occurring phosphate, for example lecithin, or condensation products of an alkene oxide with fatty acids, for example polyoxyethylene stearate, or condensation products of ethylene oxide with long chain aliphatic alcohols, for example heptadecathyl-eneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with the dispersing or wetting agent, suspending agent and one or more preservatives. Suitable dispersing or wetting agents and suspending agents are exemplified by those already mentioned above.

Additional recipients, for example sweetening, flavouring and colouring agents, may also be present.

The pharmaceutical composition of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphates, esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solutions and isotonic sodium chloride solution. In addition, fixed oils are conventionally employed as a solvent or suspending medium. For this purpose any bland fixed oil may be employed including synthetic mono- or diglycerides. In addition, fatty acids such as oleic acid find use in the preparation or injectables.

Parenteral administration is generally characterized by injection, either subcutaneously, intramuscularly or intravenously. Injectables can be prepared in conventional forms, either as liquid solutions or suspension in liquid prior to injection, or as emulsions. Suitable excipients are for example, water, saline, dextrose, glycerol, ethanol or the like. In addition, if desired, the pharmaceutical compositions to be administered may also contain minor amounts of non-toxic auxiliary substance such as wetting or emulsifying agents, pH buffering agents and the like, such as for example, sodium acetate, sorbitan monolaurate, triethanolamine oleate, etc.

The amount of active ingredient that may be combined with the carrier materials to produce a single dosage form will vary depending upon the host treated and the particular mode of administration of humans may contain from 0.5 mg to 5 gm of active agent compounded with an appropriate and convent amount of carrier material which may vary from about 5 to about 95% of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, drug combination and the severity of the particular disease undergoing therapy.

The invention is further described and illustrated in the following specific examples.

SPECIFIC DESCRIPTION OF THE MOST PREFERRED EMBODIMENTS

EXAMPLE 1

Preparation of bromo(2-pyridyl)acetonitrile

To a solution of (2-pyridyl)acetonitrile (12.0 g, 0.10 mole) in 150 ml of carbon tetrachloride, was added 18.1 g of N-bromosuccinimide (0.10 mole) at room temperature. The mixture was refluxed for 1.5 h. The resulting precipitate was removed by filtration and the solvent was removed under reduced pressure to give the crude product, which was recrystallized from hexane to yield 18.6 g (94%) of the title compound as red crystals: mp 62°–64° C.; $^1$H NMR (DMSO-d$_6$) δ8.67 (d, 1H), 7.97 (t, 1H), 7.70 (d, 1H), 7.51 (td, 1H), 5.60(s,1H) ppm; IR (KBr) ν3064, 2972, 1712, 1587, 1470, 1439, 1051, 993 cm$^{-1}$; MS m/z 196, 198 (M$^+$), 117 (M$^-$–Br); HRMS calcd for C$_7$H$_5$BrN$_2$ 195.9630, found 195.9645.

Proceeding in a similar manner, the following compound was made:

bromo(4-methoxy-3,5-dimethyl-2-pyridyl)acetonitrile:

mp 56°–57° C.; $^1$H NMR (CDCl$_3$) δ8.31 (s, 1H), 5.67 (s, 1H), 3.81 (s, 3H), 2.37 (s, 3H), 2.30 (s, 3H) ppm; $^{13}$C NMR (CDCl$_3$) δ164.84, 150.19, 149.56, 128.28, 125.59, 115.49, 60.135, 27.99, 13.51, 11.05 ppm; IR (KBr) ν3415, 2988, 2210, 1568, 1472, 1255, 997, 791 cm$^{-1}$; MS m/z 255, 257 (MH$^+$), 175 (M$^+$–Br).

EXAMPLE 2

Synthesis of [(2-benzimidazolyl)thio](2-pyridyl)acetonitrile

A mixture of 2-mercaptobenzimidazole (0.30 g, 3.0 mmole), bromo(2-pyridyl)acetonitrile (0.59 g, 3.0 mmole) and potassium carbonate (0.37 g 3.0 mmole) in 50 ml of dry N,N-dimethylformamide was heated at 60° C. for 6 h. The solvent was evaporated. The residue was dissolved in ethyl acetate, washed with water and then saturated sodium chloride solution. The organic layer was dried over magnesium sulfate and evaporated to give a solid. The crude product was further purified by column chromatography on silica gel (100% ethyl acetate) to give 66 mg (10%) of the title compound as a solid; mp 166°–167° C.; $^1$H NMR (DMSO-d$_6$) δ9.3 (m, 1H), 8.65 (m, 2H), 8.32 (m, 1H), 7.78 (br s, 4H), 4.81 (br s, 2H) ppm; IR ν2206, 1512, 1465, 1432, 1357, 1179, 740 cm$^{-1}$.

In a similar manner, by replacing 2-mercaptobenzimidazole with 2-mercaptoimidazole, the following compound was made:

[(2-imidazolyl)thio](2-pyridyl)acetonitrile:

mp 203°–204° C. (dec); $^1$H NMR (CDCl$_3$) δ8.51 (d, 1H), 7.65 (t, 1H), 7.36 (d, 2H), 7.12 (d, 1H), 7.03 (dd, 1H), 6.33 (br s, 2H) ppm, $^{13}$C NMR (CDCl$_3$) δ154.08, 148.23, 145.76, 136.84, 134.95, 134.43, 119.15, 118.40, 109.32, 96.15 ppm; IR (KBr) ν3344, 3225, 2202, 1643, 1493, 1485, 1427 cm$^{-1}$;

EXAMPLE 3

Synthesis of [(5-methoxy-2-benzimidazolyl)thio](4-methoxy-3,5-dimethyl-2-pyridyl)acetonitrile To a solution of 2-mercapto-5-methoxybenzimidazole (15.1 g, 0.14 mole) dissolved in 40 ml of 8.4% sodium hydroxide, was added 170 ml of methanol, followed by bromo(4-methoxy-3,5-dimethyl-2-pyridyl)acetonitrile(21.4 g, 0.11 mole) at room temperature. The mixture was heated to reflux for 1 h under a nitrogen atmosphere. The resulting precipitate was removed by filtration and the methanol was evaporated. The residue obtained was extracted with chloroform, and the chloroform was washed 3 times with water and dried over magnesium sulfate. After evaporation of the solvent, the crude product was recrystallized from diethyl ether to give 22.6 g (90%) of the title compound as yellowish crystals: mp 193°–197° C.; $^1$H NMR (CDCl$_3$) δ8.25 (s,1H), 7.65 (dd, 1H), 7.30 (m, 1H), 6.90 (m, 1H), 6.30 (br s, 2H), 3.95 (s, 3H), 3.75 (s, 3H), 2.50 (s, 3H), 2.20 (s, 3H) ppm.

EXAMPLE 4

Synthesis of 3-[oxo(2-pyridyl)methyl]imidazo[1,2-d]-1,2,4-thiadiazole

To a solution of [(2-imidazolyl)thio](2-pyridyl)acetonitrile (30 mg, 0.14 mmole) in 5 ml of chloroform, was added portionwise 0.12 g of 60% m-chloroperbenzoic acid (0.42 mmol). The mixture was stirred at room temperature for 10 h. The resulting mixture was washed with water and saturated sodium bicarbonate solution. The organic phase was then treated with charcoal, and filtered to give the crude product. Chromatography on silica gel (100% ethyl acetate) affords 22 mg (84%) of the title compound as a yellowish solid: mp 147°–148° C.; $^1$H NMR (CDCl$_3$) δ8.87 (d, 1H), 8.30 (m, 2H), 7.95 (m, 1H), 7.57 (m, 1H), 7.52 (m, 1H) ppm; IR (KBr) ν1700, 1660 cm$^{-1}$; MS m/z 230 (M$^+$); HRMS calcd for C$_{10}$H$_6$N$_4$OS 230.0262, found: 230.0267.

EXAMPLE 5

Synthesis of 7-methoxy-3-[(4-methoxy-3,5-dimethyl-2-pyridyl)oxomethyl]-1,2,4-thiadiazolo[4,5-a]benzimidazole and 6-methoxy-3-[(4-methoxy-3,5-dimethyl-2-pyridyl)oxomethyl]-1,2,4-thiadiazolo[4,5-a]benzimidazole To a solution of [(5-methoxy-2-benzimidazolyl)thio](4-methoxy-3,5-dimethyl-2-pyridyl)acetonitrile (5.31 g, 15 mmole) in 400 ml of chloroform, was added dropwise 60% m-chloroperbenzoic acid (8.62 g, 30 mmole) dissolved in 100 ml of chloroform at 0°–5° C. during a period of 1 h. After the addition was over, the reaction mixture was stirred at room temperature for 1 h. The resulting mixture was then washed with water and dried over magnesium sulfate. The solvent was evaporated to give the crude product. Chromatography on silica gel (ethyl acetate: hexane 1:1) yields 0.828 g (10%) of 7-methoxy-3-[(4-methoxy-3,5-dimethyl-2-pyridyl)oxomethyl]-1,2,4-thiadiazolo[4,5-a]benzimidazole as a yellowish solid and 0.828 g (10%) of 6-methoxy-3-[(4-methoxy-3,5-dimethyl-2-pyridyl)oxomethyl]-1,2,4-thiadiazolo[4,5-a]benzimidazole as a solid.

7-methoxy-3-[(4-methoxy-3,5-dimethyl-2-pyridyl)oxomethyl]-1,2,4-thiadiazolo[4,5-a]benzimidazole: mp 170°–171° C.; $^1$H NMR (DMSO-d$_6$) δ8.34 (s, 1H), 7.86 (d, 1H), 7.29 (d, 1H), 6.93 (dd, 1H), 3.84 (s, 6H), 2.42 (s, 3H), 2.31 (s, 3H) ppm; IR (KBr) ν1684, 1654 cm$^{-1}$; MS m/z 369 (M$^+$+1).

6-methoxy-3-[(4-methoxy-3,5-dimethyl-2-pyridyl)oxomethyl]-1,2,4-thiadiazolo[4,5-a]benzimidazole: mp 196°–197° C.; $^1$H NMR (DMSO-d$_6$) δ8.34 (s, 1H), 7.67 (d, 1H), 7.34 (d, 1H), 7.10 (dd, 1H), 3.84 (s, 3H), 3.74 (s, 3H), 2.44 (s, 3H), 2.31 (s, 3H) ppm; IR (KBr) ν1684 cm$^{-1}$; MS m/z 369 (M$^+$+1).

EXAMPLE 6

Synthesis of dibromo(2-pyridyl)acetonitrile

To a solution of (2-pyridyl)acetonitrile (6.0 g, 50.8 mmol) in 120 mL carbon tetrachloride was added N-bromosuccinimide (18.5 g, 104 mmol) at room temperature. The resulting mixture was heated to reflux for 2 h. After cooling, the precipitate was filtered. The carbon tetrachloride was evaporated to give 13.5 g (96%) of dibromo(2-pyridyl)acetonitrile as a dark-brown solid: mp 59°–61° C.; $^1$H NMR (CDCl$_3$) δ8.62 (d, 1H), 7.93 (d, 1H), 7.86 (dt, 1H), 7.35 (dr, 1H) ppm; $^{13}$C NMR (CDCl$_3$) δ155.23, 148.94, 138.24, 125.38, 120.55, 115.81, 30.81 ppm; HRMS calcd for C$_7$H$_4$N$_2$Br$_2$: 273.8741, found: 273.8730.

EXAMPLE 7

Synthesis of 2-butyl-1,2,4-thiadiazolo[4,5-a]benzimidazole-3(2H)-one

The mixture of 2-mercaptobenzimidazole (29.30 g, 0.195 mole) and butyl isocyanate (48.3 mL, 0.33 mole) in a 500 ml of round-bottom flask equipped with a condenser was heated to 130°–140° C. in an oil bath for 45 min. After the reaction mixture was cooled to room temperature, the solid was filtered, washed with hexane, and dried under vacuum to give 43.48 g (89%) of 1-(butylcarbamoyl)-1,3-dihydrobenzimidazole-2-thione as white crystals: mp 179°–180° C.

To a solution of 1-(butylcarbamoyl)-1,3-dihydrobenzimidazole-2-thione (39.89 g, 0.16 mole) in 250 mL of chloroform, was added 25.57 g (0.16 mole) of bromine, in 110 mL of chloroform, at 0° C. After the addition was complete, triethylamine (44.6 mL, 0.32 mole), in 80 mL of chloroform, was added dropwise to the reaction mixture. The mixture was stirred at 0° C. for an additional 4 h, and then stirred at room temperature for 14 h. The resulting mixture was washed with water and then with a 10% sodium sulfate solution. The organic layer was dried over magnesium sulfate and evaporated to give the crude product. Recrystallization from methanol gave 27.10 g (69%) of 2-butyl-1,2,4-thiadiazolo[4,5-a]benzimidazole-3(2H)-one as colourless crystals: mp 153°–154° C. (lit.: 156°–157° C., Martin et al. Tetrahedron 1983, 39, 2311).

In a similar manner, by replacing n-butyl isocyanate with other alkyl isocyanates, the following compounds are made:

2-ethyl-1,2,4-thiadiazolo[4,5-a]benzimidazole-3(2H)-one
2-isopropyl-1,2,4-thiadiazolo[4,5-a]benzimidazole-3(2H)-one
2-methyl-1,2,4-thiadiazolo[4,5-a]benzimidazole-3(2H)-one
2-phenyl-1,2,4-thiadiazolo[4,5-a]benzimidazole-3(2H)-one
2-benzyl-1,2,4-thiadiazolo[4,5-a]benzimidazole-3(2H)-one

EXAMPLE 8

Synthesis of 3-[dibromo(2-pyridyl)methyl]-1,2,4-thiadiazolo[4,5-a]benzimidazole

A mixture of 2-butyl-1,2,4-thiadiazolo[4,5-a]benzimidazole-3(2H)-one (2.0 g, 8.1 mmol) and dibromo (2-pyridyl)acetonitrile (4.91 g, 17.8 mmol) in 50 mL of dichloromethane was heated to reflux for 16 h. After cooling to room temperature, the precipitate was filtered, washed with dichloromethane and dried to give 2.76 g (80%) of the title compound as a light-brown solid: mp 195° C. (dec); $^1$H NMR (CDCl$_3$) δ8.25 (m, 2H), 7.96 (dt, 1H), 7.76 (d, 1H), 7.32 (m, 2H), 6.95 (t, 1H), 6.92 (s, 1H) ppm; $^{13}$C NMR (CDCl$_3$) δ166.08, 157.95, 150.34, 148.28, 147.71, 38.31, 128.76, 124.79, 124.58, 122.94, 121.68, 119.49, 13.97, 54.37 ppm; HRMS calcd for C$_{14}$H$_8$Br$_2$N$_4$S: 421.8836, found: 421.8850.

EXAMPLE 9

Synthesis of 3-(oxophenylmethyl)-1,2,4-thiadiazolo[4,5-a]benzimidazole

A mixture of 2-butyl-1,2,4-thiadiazolo[4,5-a]benzimidazole-3(2H)-one (6.0 g, 24.3 mmole) and benzoyl cyanide (6.36 g, 48.5 mmole) in 80 mL of dichloromethane was stirred at room temperature for 24 h. The precipitate was filtered and washed with dichloromethane. The crude product was recrystallized from acetone to give 6.48 g (96%) of 3-(oxophenylmethyl)-1,2,4-thiadiazolo[4,5-a]benzimidazole as yellow crystals: mp 190°–191° C.; $^1$H NMR (CDCl$_3$) δ8.35 (d, 3H), 7.82 (d, 1H), 7.73 (t, 1H), 7.59 (t, 2H), 7.50 (t, 1H), 7.36 (t, 1H) ppm; $^{13}$C NMR (CDCl$_3$) δ180.86, 163.69, 150.82, 146.70, 134.79, 134.34, 131.22 (2C), 129.46 (2C), 128.74, 125.82, 122.27, 119.49, 115.23 ppm; IR (KBr) v1671 cm$^{-1}$; HRMS calcd for C$_{15}$H$_9$N$_3$OS: 279.0466, found: 279.0475. Anal. Calcd for C$_{15}$H$_9$N$_3$OS: C, 64.50; H, 3.25; N, 15.04. Found: C, 63.93; H, 3.10; N, 14.53.

In a similar manner, by replacing benzoyl cyanide with pyruvonitrile, the following compound was made:

3-(1-oxoethyl)-1,2,4-thiadiazolo[4,5-a]benzimidazole: mp 180°–181° C.; $^1$H NMR (CDCl$_3$) δ8.70 (d, 1H), 7.80 (d, 1H), 7.50 (t, 1H), 7.38 (t, 1H), 2.83 (s, 3H); $^{13}$C NMR (CDCl$_3$) δ187.02, 164.15, 150.69, 147.78, 129.63, 125.82, 122.26, 119.27, 115.94, 26.74 ppm; IR (KBr) v1703 cm$^{-1}$. HRMS calcd for C$_{10}$H$_7$N$_3$OS: 217.0310, found: 217.0318. Anal. Calcd for C$_{10}$H$_7$N$_3$OS: C, 55.29; H, 3.25; N, 19.34. Found: C, 55.31; H, 3.29; N, 19.46.

In a similar manner, by replacing benzoyl cyanide with other cyanides, the following compounds are made:

3-(1-oxopropyl)-1,2,4-thiadiazolo[4,5-a]benzimidazole
3-(1-oxobutyl)-1,2,4-thiadiazolo[4,5-a]benzimidazole
3-(1-oxo-2-phenylethyl)-1,2,4-thiadiazolo[4,5-a]benzimidazole
3-(cyclopentyloxomethyl)-1,2,4-thiadiazolo[4,5-a]benzimidazole
3-(1-oxo-2-phthalimidoethyl)-1,2,4-thiadiazolo[4,5-a]benzimidazole

EXAMPLE 10

Synthesis of 3-methyl-1,2,4-thiadiazolo[4,5-a]benzimidazole

2-Butyl-1,2,4-thiadiazolo[4,5-a]benzimidazole-3(2H)-one (1.00 g, 4.04 mmol) was refluxed in 100 mL acetonitrile for 18 h. The solvent was then evaporated and the residue was recrystallized from methanol to give 0.671 g (88%) of the title compound: mp 192°–193° C.; $^1$H NMR (CDCl$_3$) δ7.81 (dm, 2H), 7.47 (td, 1H), 7.34 (td, 1H), 2.92 (s, 3H) ppm; IR (KBr) v1564, 1481, 1453, 1430, 1304, 1208, 756, 745 cm$^{-1}$; MS m/z 189 (M$^+$), 148 (M$^+$–CH$_3$CN).

In a similar manner, by replacing acetonitrile with other alkyl nitriles, the following compounds are prepared:

3-ethyl-1,2,4-thiadiazolo[4,5-a]benzimidazole
3-isopropyl-1,2,4-thiadiazolo[4,5-a]benzimidazole
3-(2-methylpropyl)-1,2,4-thiadiazolo[4,5-a]benzimidazole

EXAMPLE 11

Synthesis of 3-[4-(methoxycarbonyl)phenyl]-1,2,4-thiadiazolo[4,5-a]benzimidazole A mixture of 2-butyl-1,2,4-thiadiazolo[4,5-a]benzimidazole-3(2H)-one (0.3 g, 1.2 mole) and methyl 4-cyanobenzoate (0.41 g, 2.5 mmole) in 7 mL of dichloromethane was heated to reflux for 20 h. The precipitate was filtered and washed with dichloromethane to give 0.16 g (48%) of 3-[4-(methoxycarbonyl)phenyl]-1,2,4-thiadiazolo[4,5-a]benzimidazole as a white solid: mp 204°–206° C.; $^1$H NMR (CDCl$_3$) δ8.33 (d, 2H), 7.98 (d, 2H), 7.83 (d, 1H), 7.49 (m, 2H), 7.20 (t, 1H), 4.02 (s, 3H) ppm; $^{13}$C NMR (CDCl$_3$) δ165.96, 165.30, 151.08, 149.10,133.16, 132.55, 130.24(2C), 128.69(3C), 125.34, 121.58, 119.96, 112.01, 52.56 ppm; IR (KBr) v1729, 1508, 1448, 1275, 733 cm$^{-1}$; HRMS calcd for C$_{16}$H$_{11}$N$_3$O$_2$S, 309.0572 found 309.05719.

EXAMPLE 12

Synthesis of 3-(4-methylphenylsulfonyl)-1,2,4-thiadiazolo[4,5-a]benzimidazole

A mixture of 2-butyl-1,2,4-thiadiazolo[4,5-a]benzimidazole-3(2H)-one (10.0 g, 40.4 mmole) and p-toluenesulfonyl cyanide (14.7 g, 81.0 mmole) in 120 mL of dichloromethane was stirred at room temperature for 20 h. The precipitate was filtered and washed with dichloromethane to yield 12.2 g (91%) of 3-(4-methylphenylsulfonyl)-1,2,4-thiadiazolo[4,5-a]benzimidazole as white powder: mp 231°–234° C.; $^1$H NMR (CDCl$_3$) δ8.53 (d, 1H), 8.04 (d, 2H), 7.82 (d, 1H), 7.56–7.44 (m, 4H), 2.53 (s, 3H) ppm; $^{13}$C NMR (CDCl$_3$) δ163.72, 150.38, 147.97, 147.54, 132.48, 130.30(2C), 129.97(2C), 128.49, 126.14, 123.06, 119.70, 114.67, 21.93 ppm; IR (KBr) ν1592, 1525, 1444, 1337, 1151, 1081, 735 cm$^{-1}$; HRMS calcd for C$_{15}$H$_{11}$N$_3$O$_2$S$_2$: 329.0293, found: 329.0300. Anal. Calcd for C$_{15}$H$_{11}$N$_3$O$_2$S$_2$: C, 54.70; H, 3.37; N, 12.76. Found: C, 54.29; H, 3.14; N, 14.59.

EXAMPLE 13

Synthesis of 3-(methoxycarbonyl)-1,2,4-thiadiazolo[4,5-a]benzimidazole

A mixture of 2-butyl-1,2,4-thiadiazolo[4,5-a]benzimidazole-3(2H)-one (4.0 g, 16.2 mmole) and methyl cyanoformate (2.75 g, 32.4 mmole) in 30 mL of dichloromethane was stirred at room temperature for 21 h. The precipitate was filtered and washed with dichloromethane to give 3.36 g (84%) of 3-(methoxycarbonyl)-1,2,4-thiadiazolo[4,5-a]benzimidazole as a colourless solid: mp 208°–209° C.; $^1$H NMR (CDCl$_3$) δ8.61 (d, 1H), 7.82 (d, 1H), 7.51 (t, 1H), 7.31 (t, 1H), 4.17 (s, 3H) ppm; $^{13}$C NMR (CDCl$_3$) δ164.02, 156.51, 150.67, 140.89, 129.34, 125.93, 122.41, 119.48, 115.41, 54.04 ppm; IR (KBr) ν1733 cm$^{-1}$; HRMS calcd for C$_{10}$H$_7$N$_3$O$_2$S 233.0259, found 233.0262. Anal. Calcd. for C$_{10}$H$_7$N$_3$O$_2$S: C, 51.50; H, 3.02; N, 18.02. Found: C, 51.41; H, 2.89; N, 18.16.

In a similar manner, by replacing methyl cyanoformate with other cyanoformates, the following compounds are made:

3-(ethoxycarbonyl)-1,2,4-thiadiazolo[4,5-a]benzimidazole
3-(butoxycarbonyl)-1,2,4-thiadiazolo[4,5-a]benzimidazole
3-(isopropoxycarbonyl)-1,2,4-thiadiazolo[4,5-a]benzimidazole
3-[(benzyloxy)carbonyl]-1,2,4-thiadiazolo[4,5-a]benzimidazole
3-[(cyclopentyloxy)carbonyl]-1,2,4-thiadiazolo[4,5-a]benzimidazole

EXAMPLE 14

Synthesis of 3-(2-pyridyl)-1,2,4-thiadiazolo[4,5-a]benzimidazole

A mixture of 2-butyl -1,2,4-thiadiazolo[4,5-a]benzimidazole-3(2H)-one (15.0 g, 60.7 mmole) and 2-cyanopyridine (13.3 g, 0.13 mole) in 150 mL of dichloromethane was stirred at room temperature for 72 h. The precipitate was filtered and washed with dichloromethane to give 10.4 g (68%) of 3-(2-pyridyl)-1,2,4-thiadiazolo[4,5-a]benzimidazole as a white solid: mp 173°–174° C.; $^1$H NMR (CDCl$_3$) δ8.90 (d, 1H), 8.70 (d, 1H), 8.30 (d, 1H), 7.99 (t, 1H), 7.80 (d, 1H), 7.57 (t, 1H), 7.47 (t, 1H), 7.37 (t, 1H) ppm; $^{13}$C NMR (CDCl$_3$) δ166.10, 151.09, 150.11, 148.74, 147.73, 137.38, 130.50, 125.85, 125.24, 124.52, 121.41, 119.11, 116.33 ppm; IR (KBr) ν3419, 3054, 1611, 1587, 1501, 1463, 1446, 727 cm$^{-1}$. HRMS calcd for C$_{13}$H$_8$N$_4$S 252.0470, found 252.0882. Anal. Calcd for C$_{13}$H$_8$N$_4$S: C, 61.89; H, 3.20; N, 22.21. Found: C, 61.48; H, 3.30; N, 22.24.

EXAMPLE 15

Synthesis of 3-amino-1,2,4-thiadiazolo[4,5-a]benzimidazole

To a cooled solution of 2-butyl-1,2,4-thiadiazolo[4,5-a]benzimidazole-3(2H)-one (2.00 g, 8.08 mmole) in 25 mL dichloromethane, cyanamide (0.728 g, 16.2 mmole) Was added in one portion and the mixture was stirred for 48 h at room temperature. The resulting precipitate was filtered, slurried in methanol and subsequently washed with dichloromethane to give 1.01 g (66%) of 3-amino-1,2,4-thiadiazolo[4,5-a]benzimidazole as colourless crystals: mp 255°–256° C.; $^1$H NMR (DMSO-d$_6$) δ 8.23 (d, 1H), 7.71 (d, 1H), 7.43 (t, 1H), 7.54 (s, 2H), 7.32 (t, 1H) ppm; IR (KBr) ν3302, 3151, 1661, 1577, 1487, 1473, 1251, 1207, 810 cm$^{-1}$; HRMS calcd for C$_8$H$_6$N$_4$S 190.0313, found 190.0293. Anal. Calcd for C$_8$H$_6$N$_4$S: C, 50.51; H, 3.18; N, 29.45. Found: C, 50.26; H, 3.26; N, 29.38.

EXAMPLE 16

Synthesis of 3-bromo-1,2,4-thiadiazolo[4,5-a]benzimidazole

A mixture of 2-butyl-1,2,4-thiadiazolo[4,5-a]benzimidazole-3(2H)-one (5.0 g, 20.2 mmole) and cyanogen bromide (4.28 g, 40.4 mmole) in 100 mL of dichloromethane was stirred at room temperature for 26 h. The precipitate was filtered and washed with dichloromethane to yield 4.18 g (81%) of 3-bromo-1,2,4-thiadiazolo[4,5-a]benzimidazole as a white powder: mp 189°–190° C.; $^1$H NMR (CDCl$_3$) δ8.23 (d, 1H), 7.82 (d, 1H), 7.52 (t, 1H), 7.42 (d, 1H)ppm; $^{13}$C NMR (1:1 CDCl$_3$:DMSO-d$_6$): δ162.78, 149.67, 129.22, 125.53, 122.25, 119.48, 117.25, 111.27 ppm; IR (KBr): ν3025, 2925, 1601, 1493, 1451, 1028, 757, 701 cm$^{-1}$; HRMS calcd for C$_8$H$_4$N$_3$SBr 252.9309, found 252.9307. Anal. Calcd for C$_8$H$_4$N$_3$SBr: C, 37.81; H, 1.59; N, 16.54. Found: C, 37.44; H, 1.33; N, 16.57.

In a similar manner, by replacing cyanogen bromide with other cyanogen halides, the following compounds are made:

3-iodo-1,2,4-thiadiazolo[4,5-a]benzimidazole
3-chloro-1,2,4-thiadiazolo[4,5-a]benzimidazole

EXAMPLE 17

Synthesis of 3-[oxo(2-pyridyl)methyl]-1,2,4-thiadiazolo[4,5-a]benzimidazole

To a solution of 3-[dibromo(2-pyridyl)methyl]-1,2,4-thiadiazolo[4,5-a]benzimidazole (2.02 g, 4.76 mmol) in 75 mL tetrahydrofuran was added a solution of silver nitrate (0.890 g, 5.24 mmol) in 75 mL water. The suspension was stirred for 2 days and then basified to pH 6 with aqueous sodium bicarbonate. After the addition of 1 mL saturated aqueous sodium chloride, the mixture was filtered on celite and the celite was washed with ethyl acetate. After extraction with water, the ethyl acetate was dried and evaporated to give a crude residue which was purified by flash chromatography using a mixture of chloroform/methanol 10:0.1 as the eluent. 1.05 g (78%) of the title compound was obtained as a yellow solid: mp 182°–186° C. (dec); $^1$H NMR (CDCl$_3$) δ8.85 (m, 1H), 8.31 (dr, 1H), 8.19 (d, 1H), 8.01 (td, 1H), 7.83 (d, 1H), 7.63 (ddd, 1H), 7.50 (ddd, 1H), 7.35 (ddd, 1H) ppm; IR (film) 1673, 1511, 1444, 1235, 1057, 879, 733 cm$^{-1}$; MS m/z 280 (M$^+$), 148 (M$^+$–(2-pyridyl)C(O)CN).

EXAMPLE 18

Synthesis of 3-[bis(ethoxycarbonyl)methyl]-1,2,4-thiadiazolo[4,5-a]benzimidazole A mixture of 3-bromo-1,2,4-thiadiazolo[4,5-a]benzimidazole (0.2 g, 0.78 mmole), diethyl malonate (0.15 g, 0.94 mmol) and triethylamine (0.13 mL, 0.94 mmole) in 8 mL of THF was refluxed under a nitrogen atmosphere for 36 h. The resulting mixture was extracted with ethyl acetate, washed with water and 10% aqueous sodium sulfate. The organic layer was dried over magnesium sulfate to give the crude product, which was purified by flash chromatography (35% ethyl acetate: 65% hexane) to afford 0.14 g (54%) of the title compound as a yellow oil:

$^1$H NMR (CDCl$_3$) δ9.48 (s, 1H), 8.06 (d, 1H), 7.63 (d, 1H), 7.34–7.31 (m, 2H), 4.39 (q, 4H), 1.35 (t, 6H) ppm; IR (film) 1748 cm$^{-1}$. HRMS calcd for C$_{15}$H$_{15}$N$_3$O$_4$S 333.0783, found 333.0794.

EXAMPLE 19

Synthesis of 3-methoxy-1,2,4-thiadiazolo[4,5-a]benzimidazole

To a cooled mixture of 3-bromo-1,2,4-thiadiazolo[4,5-a]benzimidazole (4.55 g, 17.9 mmole) in 50 mL of methanol, sodium methoxide (0.967 g, 17.9 mmole) was added in one portion and stirred for 4 h at room temperature. The reaction mixture was evaporated to dryness under vacuum and the residue was taken-up in ethyl acetate and washed with water. The organic layer was dried with sodium sulfate, filtered and evaporated to yield 3.64 g (94%) of 3-methoxy-1,2,4-thiadiazolo[4,5-a]benzimidazole as colourless crystals: mp 172°–175° C.; $^1$H NMR (CDCl$_3$) δ7.83 (d, 1H), 7.75 (d, 1H), 7.42 (t, 1H), 7.27 (t, 1H), 4.32 (s, 3H) ppm; $^{13}$C NMR (CDCl$_3$) δ163.2, 150.3, 148.1, 128.2, 124.9, 121.8, 119.2, 111.7, 57.5 ppm; IR (KBr) v3418, 2942, 1595, 1492, 1404, 1275, 1255, 1206, 1083, 755 cm$^{-1}$. Anal. Calcd for C$_9$H$_7$N$_3$OS: C, 52.67; H, 3.44; N, 20.49. Found: C, 52.28; 3.36; N, 20.45.

In a similar manner, by replacing sodium methoxide with other metal alkyloxides, the following compounds are made:

3-ethoxy-1,2,4-thiadiazolo[4,5-a]benzimidazole
3-propoxy-1,2,4-thiadiazolo[4,5-a]benzimidazole
3-isopropoxy-1,2,4-thiadiazolo[4,5-a]benzimidazole
3-butoxy-1,2,4-thiadiazolo[4,5-a]benzimidazole
3-tert-butoxy-1,2,4-thiadiazolo[4,5-a]benzimidazole
3-(cyclopentyloxy)-1,2,4-thiadiazolo[4,5-a]benzimidazole

EXAMPLE 20

Synthesis of 3-(dimethylamino)-1,2,4-thiadiazolo[4,5-a]benzimidazole

To a cooled mixture of 3-bromo-1,2,4-thiadiazolo[4,5-a]benzimidazole (15.44 g, 0.0603 mole) in 100 mL dichloromethane, dimethylamine (40% solution in water) (5.44 g, 0.121 mole) was added dropwise. The reaction mixture was allowed to stir for 16 h at room temperature. It was then diluted with dichloromethane, washed with water, dried with sodium sulfate and evaporated under vacuum to give 10.47 g (80%) of 3-(dimethylamino)-1,2,4-thiadiazolo[4,5-a]benzimidazole as colourless crystals: mp 102°–104° C.; $^1$H NMR (CDCl$_3$) δ7.74 (t, 2H), 7.41 (t, 1H), 7.27 (t, 1H), 3.06 (s, 6H) ppm. Anal. Calcd for C$_{10}$H$_{10}$N$_4$S: C, 55.03; H, 4.62; N, 25.69. Found: C, 54.53; H, 4.90; N, 25.50.

In a similar manner, by replacing dimethylamine with other amines, the following compounds were made:

3-(ethylamino)-1,2,4-thiadiazolo[4,5-a]benzimidazole: mp 164.5°–165° C. (dec); $^1$H NMR (CDCl$_3$) δ7.78 (m, 2H), 7.65 (d, 1H), 7.43 (t, 1H), 7.21 (t, 1H) 3.68 (q, 2H), 1.45 (t, 3H) ppm.

3-(1-pyrrolyl)-1,2,4-thiadiazolo[4,5-a]benzimidazole: mp 118°–119° C.; $^1$H NMR (CDCl$_3$) δ7.77 (t, 2H), 7.43 (t, 1H), 7.28 (t, 1H), 3.71 (m, 4H), 2.07 (m, 4H) ppm.

3-(4-morpholinyl)-1,2,4-thiadiazolo[4,5-a]benzimidazole: mp 140°–142° C.; $^1$H NMR (CDCl$_3$) δ7.78 (d, 1H), 7.60 (d, 1H), 7.45 (t, 1H), 7.32 (t, 1H), 3.99 (m, 4H), 3.48 (m, 4H) ppm.

3-(1-piperazinyl)-1,2,4-thiadiazolo[4,5-a]benzimidazole: mp 116°–118° C.; $^1$H NMR (CDCl$_3$) δ7.76 (d, 1H), 7.63 (d, 1H), 7.42 (t, 1H), 7.30 (t, 1H), 3.41 (m, 4H), 3.15 (t, 4H), 2.00 (br s, 1H) ppm.

3-(4-methyl-1-piperazinyl)-1,2,4-thiadiazolo[4,5-a]benzimidazole: mp 158°–158.5° C.; $^1$H NMR (CDCl$_3$) δ7.77 (d, 1H), 7.64 (d, 1H), 7.42 (t, 1H), 7.32 (t, 1H), 3.49 (m, 4H), 2.70 (m, 4H), 2.43 (s, 3H) ppm.

3-[[2-(methoxycarbonyl)methyl]amino]-1,2,4-thiadiazolo[4,5-a]benzimidazole: mp 196°–197° C. Anal. Calcd for C$_{11}$H$_{10}$N$_4$O$_2$S: C, 50.37; H, 3.84; N, 21.36. Found: C, 50.13; H, 3.96; N, 21.26.

In a similar manner, by replacing dimethylamine with other nucleophilic amines, the following compound is made:

3-(methylamino)-1,2,4-thiadiazolo[4,5-a]benzimidazole

EXAMPLE 21

Synthesis of 3-[(hydroxyimino) phenylmethyl]-1,2,4-thiadiazolo[4,5-a]benzimidazole To a solution of 0.5 g (1.79 mmol) of 3-(oxophenylmethyl)-1,2,4-thiadiazolo[4,5-a]benzimidazole in 7 mL of ethanol was added 0.5 mL (6.46 mmol) of pyridine and 0.5 g (7.20 mmol) of hydroxylamine hydrochloride. The mixture was refluxed for overnight. The precipitate was collected by filtration, and washed with methanol and dichloromethane to give the crude product, which was recrystallized from methanol to yield 0.47 g (89%) of the title compound as white crystals. mp 247° C.; $^1$H NMR (DMSO-d$_6$) δ11.89 (s, 1H), 7.81 (d, 1H), 7.73 (dd, 2H), 7.45–7.53 (m, 5H), 7.32 (t, 1H) ppm; $^{13}$C NMR (CDCl$_3$) δ168.25, 155.24, 150.52, 147.95, 136.94, 135.67, 134.30(2C), 133.03, 131.52(2C), 130.35, 127.26, 124.28, 116.91 ppm; IR (KBr) δ2731, 1549, 1475, 1450, 1251, 1194, 983, 753, 736 cm$^{-1}$. HRMS calcd for C$_{15}$H$_{10}$N$_4$OS 294.0575, found 294.0583.

EXAMPLE 22

Synthesis of 3-(1-hydroxyethyl)-1,2,4-thiadiazolo[4,5-a]benzimidazole

To a suspension of 3-(1-oxoethyl)-1,2,4-thiadiazolo[4,5-a]benzimidazole (729 mg, 3.36 mmol) in 200 mL methanol, was added sodium borohydride (140 mg, 3.69 mmol). The mixture was stirred for 30 min and 0.1 mL of water was added. The methanol was evaporated and the residue was partitioned between ethyl acetate and 0.1M hydrochloric acid. The aqueous phase was extracted with ethyl acetate. The organic phases were combined, washed twice with brine, dried and evaporated. The crude residue was purified by chromatography using chloroform/methanol to give 3-(1-hydroxyethyl)-1,2,4-thiadiazolo[4,5-a]benzimidazole. mp 174°–175° C.; $^1$H NMR (CDCl$_3$) δ8.05 (d, 1H), 7.80 (d, 1H), 7.47 (td, 1H), 7.36 (td, 1H), 5.39 (q, 1H), 2.76 (d, 1H), 1.84 (d, 3H) ppm; IR (KBr) v3136, 1544, 1494, 1478, 1451, 1374, 1250, 1200, 1123, 1103, 1093, 752, 729, 711 cm$^{-1}$; MS m/z 219 (M$^+$), 148 (M$^+$–CH$_3$CH(OH)CN).

EXAMPLE 23

Synthesis of 3-carboxy-1,2,4-thiadiazolo[4,5-a] benzimidazole

To a 6 mL solution of 1N NaOH, 3-(methoxycarbonyl)-1,2,4-thiadiazolo[4,5-a]benzimidazole (1.0 g, 4.3mmole) in 6 mL of dioxane, was added. The reaction mixture was stirred at room temperature until completion. The resulting mixture was then acidified with 3N HCl to pH ~2.0, and stirred at room temperature for an additional 0.5 h. The solid was filtered, washed with water, and dried under vacuum at 60° C. for 24 h to yield 0.74 g (78%) of the title compound as a colourless solid: mp 184°–185° C. (dec); $^1$H NMR (DMSO-$d_6$) δ13.79 (br s, 1H), 8.59 (d, 1H), 7.78 (d, 1H), 7.51 (t, 1H), 7.40 (t, 1H); IR (KBr) v3435, 1705 cm$^{-1}$; MS m/z 193 (M$^+$–OH), 175 (M$^+$–CO$_2$).

EXAMPLE 24

Synthesis of sodium 3-carboxylato-1,2,4-thiadiazolo[4,5-a] benzimidazole

To a suspension of 3-carboxy-1,2,4-thiadiazolo[4,5-a] benzimidazole (10.00 g, 45.62 mmol) in methanol (150 ml) and water (100 ml), 1M NaOH (45.6 ml) was added over a period of 1 h. After 4 h, the solution turned clear and the methanol was removed under reduced pressure. The aqueous solution was extracted with chloroform, the aqueous phase was freeze-dried to give the title compound (10.4 g, 95%) as a white solid: mp 225°–227° C.; $^1$H NMR (DMSO-$d_6$) δ7.68 (d, 1H), 7.05 (d, 1H), 6.95 (t, 1H), 6.80 (t, 1H) ppm; $^{13}$C NMR (DMSO-$d_6$) δ167.20, 161.76, 149.68, 148.84, 129.52, 126.23, 122.74, 118.37, 116.06 ppm; IR (KBr) v3395, 3243, 1663, 1641, 1522, 1443, 1334, 827, 729 cm$^{-1}$.

EXAMPLE 25

Preparation of 3-(4-methyl-1-piperazinyl)-1,2,4-thiadiazolo[4,5-a]benzimidazole dihydrochloride To a clear solution of 3-(4-methyl-1-piperazinyl)-1,2,4-thiadiazolo[4,5-a]benzimidazole (6.07 g, 22.21 mmol) in 100 ml of dichloromethane, hydrogen chloride gas was bubbled through for 40 min. The solution became turbid with time. The suspension was filtered and dried under vacuum to give the title compound as a fine white powder 7.60 g (99%). mp 252° C. (dec); $^1$H NMR (DMSO-$d_6$ & D$_2$O) δ7.85 (d, 2H), 7.60 (t, 1H), 7.51 (t, 1H), 3.86 (m, 2H), 3.56 (m, 6H), 2.91 (s, 3H) ppm; $^{13}$C NMR (DMSO-$d_6$ & D$_2$O) δ164.39, 148.80, 144.27, 126.92, 126.12, 123.41, 117.08, 113.20, 51.19, 45.87, 42.32 ppm; IR (KBr) v3420, 1606, 1571, 1475, 1461, 1225, 981, 761 cm$^{-1}$.

EXAMPLE 26

Preparation of 2-butylimidazo[1,2-d]-1,2,4-thiadiazole-3(2H)-one

2-Mercaptoimidazole (24.39 g, 0.244 mole) and butyl isocyanate (48.3 g, 0.487 mole) were combined in a round-bottom flask and heated to 50° C. for 30 min or until the reaction was complete by TLC. The reaction mixture was then cooled to room temperature and the solidified mass was triturated with 50 mL of hexane for 30 min. The beige solid was filtered, washed with a minimum amount of hexane and dried under reduced pressure to yield 44.96 g (93%) of 1-(butylcarbamoyl)-1,3-dihydroimidazole-2-thione as beige crystals: mp 66°–68° C.

To solution containing 1-(butylcarbamoyl)-1,3-dihydroimidazole-2-thione (4.73 g, 23.7 mmole) suspended in 15 mL of dichloromethane cooled to 0° C. under a nitrogen atmosphere, was added bromine (3.79 g, 23.7 mmole) dissolved in 15 mL of dichloromethane, in a dropwise manner. After the addition was complete, triethylamine (4.81 g, 47.5 mmole) dissolved in 15 mL dichloromethane was added such that the temperature of the reaction mixture never exceeded 0° C. The reaction mixture was maintained at 0° C. for an additional 2 h and then stirred for 16 h at room temperature. It was then diluted with 150 mL of dichloromethane and washed twice with water and once with a saturated sodium chloride solution. The organic layer was then dried over magnesium sulfate and evaporated to dryness to yield 4.30 g (92%) of 2-butylimidazo[1,2-d]-1,2,4-thiadiazole-3(2H)-one as an off-white powder: mp 142°–143° C.; $^1$H NMR (CDCl$_3$) δ7.40 (d, 1H), 7.20 (d, 1H), 3.79 (t, 2H), 1.73 (m, 2H), 1.40 (m, 2H), 0.957 (t, 3H) ppm; IR (KBr) v1702 cm$^{-1}$.

In a similar manner, by replacing butyl isocyanate with other selected isocyanates, the following compounds are made:

2-methylimidazo[1,2-d]-1,2,4-thiadiazole-3(2H)-one
2-ethylimidazo[1,2-d]-1,2,4-thiadiazole-3(2H)-one
2-propylimidazo[1,2-d]-1,2,4-thiadiazole-3(2H)-one
2-isopropylimidazo[1,2-d]-1,2,4-thiadiazole-3(2H)-one
2-pentylimidazo[1,2-d]-1,2,4-thiadiazole-3(2H)-one
2-hexylimidazo[1',2-d]-1,2,4-thiadiazole-3(2H)-one
2-cyclohexylimidazo[1,2-d]-1,2,4-thiadiazole-3(2H)-one
2-benzyl imidazo[1,2-d]-1,2,4-thiadiazole -3(2H)-one

EXAMPLE 27

Synthesis of 3-(1-oxoethyl)imidazo[1,2-d]-1,2,4-thiadiazole-3(2H)-one

To a cooled solution of 2-butylimidazo[1,2-d]-1,2,4-thiadiazole-3(2H)-one (2.49 g, 12.6 mmole) in 5 mL of dichloromethane, pyruvonitrile (1.74 g, 25.2 mmole) was added dropwise and allowed to stir for 24 h. The precipitate was then collected by filtration, washed with dichloromethane and evaporated under reduced pressure to yield 0.662 g (31%) of 3-(1-oxoethyl) imidazo[1,2-d]-1,2,4-thiadiazole-3(2H)-one as yellow-green crystals: mp 142°–144° C.; $^1$H-NMR (CDCl$_3$) δ8.23 (s, 1H), 7.51 (s, 1H), 2.78 (s, 3H) ppm; IR (KBr) v3436, 3168, 3106, 1516, 1408, 1363, 1229, 1136, 730 cm$^{-1}$. Anal. Calcd for C$_6$H$_5$N$_3$SO: C, 43.11; H, 3.01; N, 25.13. Found: C, 43.11; H, 2.91; N, 25.27.

In a similar manner, by replacing pyruvonitrile with benzoyl cyanide, the following compound was made:

3-(oxophenylmethyl)imidazo[1,2-d]-1,2,4-thiadiazole-3 (2H)-one: mp 166°–168° C.; $^1$H NMR (CDCl$_3$) δ8.44 (d, 2H), 8.40 (s, 1H), 7.70 (d, 1H), 7.58 (t, 3H) ppm.

In a similar manner, by replacing pyruvonitrile with other selected cyanide or nitriles, the following compounds are made:

3-(1-oxopropyl)imidazo[1,2-d]-1,2,4-thiadiazole-3(2H)-one
3-(1-oxobutyl)imidazo[1,2-d]-1,2,4-thiadiazole-3(2H)-one
3-(1-oxopentyl)imidazo[1,2-d]-1,2,4-thiadiazole-3(2H)-one
3-(1-oxohexyl)imidazo[1,2-d]-1,2,4-thiadiazole-3(2H)-one
3-(cyclopentyloxomethyl)imidazo[1,2-d]-1,2,4-thiadiazole-3(2H)-one
3-(1-oxo-2-phthalimidoethyl)imidazo[1,2-d]-1,2,4-thiadiazole-3(2H)-one

EXAMPLE 28

Synthesis 3-(methoxycarbonyl)imidazo[1,2-d]-1,2,4-thiadiazole

To a cooled solution of 2-butylimidazo[1,2-d]-1,2,4-thiadiazole-3(2H)-one (2.95 g, 15.0 mmole) in 25 mL dichloromethane, methyl cyanoformate (2.54 g, 30 mmole) was added dropwise and the mixture was stirred for 16 h at room temperature. The precipitate was filtered and subsequently washed with dichloromethane to give 2.18 g (80%) of 3-(methoxycarbonyl)imidazo[1,2-d]-1,2,4-thiadiazole as colourless crystals: mp 164.5°–165° C.; $^1$H NMR (CDCl$_3$) δ8.13 (s, 1H), 7.51 (s, 1H), 4.11 (s, 3H) ppm; IR (KBr) δ3440, 1737, 1527, 1253, 1071 cm$^{-1}$. Anal. Calcd for C$_6$H$_5$N$_3$O$_2$S: C, 39.34; H, 2.75; N, 22.94. Found: C, 39.41; H, 2.51; N, 22.94.

In a similar manner, by replacing methyl cyanoformate with other cyanoformates, the following compounds are made:

3-(ethoxycarbonyl)imidazo[1,2-d]-1,2,4-thiadiazole
3-(propoxycabonyl)imidazo[1,2-d]-1,2,4-thiadiazole
3-(butoxycabonyl)imidazo[1,2-d]-1,2,4-thiadiazole
3-(isopropoxycarbonyl)imidazo[1,2-d]-1,2,4-thiadiazole
3-[(pentyloxy)cabonyl]imidazo[1,2-d]-1,2,4-thiadiazole
3-[(cyclopentyloxy)cabonyl]imidazo[1,2-d]-1,2,4-thiadiazole
3-[(benzyloxy)cabonyl]imidazo[1,2-d]-1,2,4-thiadiazole

EXAMPLE 29

Synthesis of 3-bromoimidazo[1,2-d]-1,2,4-thiadiazole

To a cooled solution of 2-butylimidazo[1,2-d]-1,2,4-thiadiazole-3(2H)-one (4.78 g, 0.0242 mole) in 25 mL dichloromethane, cyanogen bromide (5.13 g, 0.0482 mole) was added in one portion and the mixture was stirred for 16 h at room temperature. The precipitate was filtered, slurried in 10 mL of methanol and subsequently washed with dichloromethane to give 4.45 g (90%) of 3-bromoimidazo[1,2-d]-1,2,4-thiadiazole as a colourless powder: mp 220° C. (dec); MS m/z 205, 203 (M$^+$). Anal. Calcd for C$_4$H$_2$N$_3$SBr.½ H$_2$O: C, 22.55; H, 1.42; N, 19.72; O, 3.75; S, 15.02; Br, 37.50. Found: C, 22.79; H, 1.41; N, 19.42; O, 2.67; S, 14.61; Br, 38.20.

In a similar manner, by replacing cyanogen bromide with other cyanogen halides, the following compounds are made:

3-iodoimidazo[1,2-d]-1,2,4-thiadiazole
3-chloroimidazo[1,2-d]-1,2,4-thiadiazole

EXAMPLE 30

Synthesis of 3-methylsulfonyl-1,2,4-thiadiazolo[4,5-a]benzimidazole

To a solution of 3-methylthio-1,2,4-thiadiazolo[4,5-a]benzimidazole (100 mg, 0.45 mmole) in 10 mL dichloromethane was added m-chloroperbenzoic acid (287 mg, 0.95 mmole). The mixture was stirred at room temperature and the starting material was converted to the sulfoxide after a few hours; it was then further oxidized to the sulfone after 18 h. The solvent was than evaporated and the residue purified by chromatography using chloroform/methanol 10:0.1 as the eluent to yield 50 mg (44%) of 3-methylsulfonyl-1,2,4-thiadiazolo[4,5-a]benzimidazole as white solid: mp 203°–207° C. (dec); $^1$H NMR (CDCl$_3$) δ8.31 (d, 1H), 7.84 (d, 1H), 7.54 (ddd, 1H), 7.43 (td, 1H), 3.63 (s,3H) ppm; IR (KBr) v1530, 1487, 1444,1324, 1315, 1193, 1147, 1141, 735 cm$^{-1}$, MS m/z 253 (M$^+$), 174 (M$^+$–CH$_3$SO$_2$), 148 (M$^+$–CH$_3$SO$_2$CN).

EXAMPLE 31

Acid stability of 7-methoxy-3-[(4-methoxy-3,5-dimethyl-2-pyridyl)oxomethyl]-1,2,4-thiadiazolo[4,5-a]benzimidazole To examine acid stability of the captioned compound, the compound was dissolved in a minimum volume of methanol and the resulting solution was added to a 6 molar solution of hydrochloric acid. The compound was found to be very stable in acid and was totally recovered after stirring for 48 hours at room temperature. Omeprazole, on the other hand, underwent complete decomposition in a few minutes under the above conditions. 1,2,4-Thiadiazole derivatives are superior to omeprazole as a direct thiol trapping agent in acidic medium because they are stable in acid.

EXAMPLE 32

Reaction of 3-[(4-methoxy-3,5-dimethyl-2-pyridyl)oxomethyl]-1,2,4-thiadiazolo[4,5-a]benzimidazole with 3-mercaptopropionic acid.

To a suspension of 250 mg of 3-[(4-methoxy-3,5-dimethyl-2-pyridyl)oxomethyl]-1,2,4-thiadiazolo[4,5-a]benzimidazole in 125 mL methanol and 38 mL 0.1M hydrochloric acid was added 161 µL of 3-mercaptopropionic acid. After complete degradation of the starting material, the mixture was neutralized to pH 6 with aqueous sodium bicarbonate and extracted with ethyl acetate. The ethyl acetate was dried on anhydrous magnesium sulfate and evaporated. The crude material was purified by chromatography to give 93 mg of 2-imino-2-(2-mercapto-1-benzimidazolyl)-1-(4-methoxy-3,5-dimethyl-2-pyridyl)ethanone, 65 mg of 2-mercaptobenzimidazole and 61 mg of methyl 2-(4-methoxy-3,5-dimethyl-2-pyridyl)-2-oxoacetate. 2-Imino-2-(2-mercapto-1-benzimidazolyl)-1-(4-methoxy-3,5-dimethyl-2-pyridyl)ethanone: $^1$H NMR (CDCl$_3$) δ10.55 (br s, 1H, NH or SH), 10.35 (br s, 1H, NH or SH), 8.10 (d, 1H, J=7 Hz, ArH), 7.80 (s, 1H, H6 of pyridyl), 7.35–7.20 (m, 2H, 2×ArH), 7.10 (d, 1H, J=7.9 Hz, ArH), 3.75 (s, 3H, OCH$_3$), 2.60 (s, 3H, ARCH$_3$), 2.15 (s, 3H, ArCH$_3$) ppm; IR (KBr) v3262, 1691, 1635, 1502, 1458, 1396, 1328, 1272, 1247, 1004, 746 cm$^{-1}$; MS (electrospray) m/z 341 (MH$^+$), 191 (MH$^+$–2-mercaptobenzimidazole). 2-Mercaptobenzimidazole: the material was found to be identical to an authentic sample purchased from Aldrich Chemical Co. by $^1$H NMR, IR and TLC. Methyl 2-(4-methoxy-3,5-dimethyl-2-pyridyl)-2-oxoacetate: $^1$H NMR (CDCl$_3$) δ8.45 (s, 1H, ArH), 4.1 (s, 3H, OCH$_3$), 3.85 (s, 3H, OCH$_3$), 2.65 (s, 3H, ArCH$_3$), 2.4 (s, 3H, ArCH$_3$) ppm; IR (KBr) v1747, 1703, 1468, 1394, 1310, 1242, 1206, 1120, 1004, 740 cm$^{-1}$; MS m/z 224 (M$^+$+H), 164 (M$^+$–CO$_2$Me), 136 (M$^+$–CO$_2$Me–CO).

EXAMPLE 33

Reaction of 3-(dimethylamino)-1,2,4-thiadiazolo[4,5-a]benzimidazole with phenethyl mercaptan.

To a solution of 23 mg of 3-(dimethylamino)-1,2,4-thiadiazolo[4,5-a]benzimidazole in 10 mL of methanol was added 360 µL of phenethyl mercaptan. After 1 min, the reaction is complete. The solvent was evaporated and the crude material was purified by chromatography to give 15 mg of N$^1$, N$^1$-dimethyl-2-mercapto-1-benzimidazolylamidine: $^1$H NMR (DMSO-d$_6$) δ7.3–7.0 (m, 4H, 4×ArH), 3.35 (br s, 2H, NH, SH), 2.88 (s, 6H, 2×NCH$_3$) ppm; IR (KBr) v3210, 1641, 1475, 1452, 1407, 1319 cm$^{-1}$; MS m/z 220 (M$^+$), 150 (M$^+$–Me$_2$NC=NH).

EXAMPLE 34

Reaction of 3-bromo-1,2,4-thiadiazolo[4,5-a]benzimidazole with phenethyl mercaptan.

To a suspension of 500 mg of 3-bromo-1,2,4-thiadiazolo[4,5-a]benzimidazole in 50 mL methanol was added 790 µL of phenethyl mercaptan. The solid rapidly dissolves. After completion of the reaction, the solvent was evaporated and the residue purified by chromatography to give 296 mg of 2-mercapto-1-benzimidazolecarbonitrile:=H NMR (DMSO-d$_6$) δ12.85 (br s, 1H, SH), 7.5–7.2 (m, 4H, 4×ArH) ppm; IR (KBr) v2259, 1509, 1459, 1303, 1189, 752 cm$^{-1}$; MS m/z 175 (M$^+$), 150 (M$^+$–CN).

EXAMPLE 35

Reaction of 3-methoxy-1,2,4-thiadiazolo[4,5-a]benzimidazole with phenethyl mercaptan.

To a solution of 23 mg of 3-methoxy-1,2,4-thiadiazolo[4,5-a]benzimidazole in 10 mL of methanol was added 376 μL of phenethyl mercaptan. After 1 min, the reaction is complete. The methyl 2-mercapto-1-benzimidazolecarboximidate was identified as the major reaction product of the reaction: $^1$H NMR (DMSO-d$_6$) δ13.45 (br s, 1H, SH or NH), 9.8 (s, 1H, NH or SH), 7.7 (d, 1H, J=8 Hz, ArH), 7.35–7.2 (m, 3H, 3×ArH), 3.95 (s, 3H, OCH$_3$) ppm; IR (KBr) v3437, 3095, 1679, 1450, 1440, 1376, 1193, 735 cm$^{-1}$; MS m/z=207 (M$^+$), 150 (M$^+$–MeOC=NH).

EXAMPLE 36

Reaction of 3-(oxophenylmethyl)-1,2,4-thiadiazolo[4,5-a]benzimidazole with phenethyl mercaptan To a suspension of 26 mg of 3-(oxophenylmethyl)-1,2,4-thiadiazolo[4,5-a]benzimidazole in 10 mL methanol was added 31 μL of phenethyl mercaptan. It was found that the substrate undergoes complete conversion to 2-mercaptobenzimidazole by comparing with an authentic sample of 2-mercaptobenzimidazole purchased from Aldrich Chemical Co.

EXAMPLE 37

Reaction of 3-[hydroxy(4-methoxy-3,5-dimethyl-2-pyridyl)methyl]-1,2,4-thiadiazolo[4,5-a]benzimidazole with phenethyl mercaptan.

To a suspension of 25 mg of 3-[hydroxy(4-methoxy-3,5-dimethyl-2-pyridyl)methyl]-1,2,4-thiadiazolo[4,5-a]benzimidazole in 10 mL methanol was added 250 μL of phenethyl mercaptan. It was found that the substrate undergoes complete conversion to 2-mercaptobenzimidazole by comparing with an authentic sample of 2-mercaptobenzimidazole purchased from Aldrich Chemical Co.

EXAMPLE 38

Reaction of 3-[(4-methylphenyl)sulfonyl]-1,2,4-thiadiazolo[4,5-a]benzimidazole with phenethyl mercaptan.

To a suspension of 31 mg of 3-[(4-methylphenyl)sulfonyl]-1,2,4-thiadiazolo[4,5-a]benzimidazole in 10 mL methanol was added 313 μL of phenethyl mercaptan. It was found that the substrate undergoes complete conversion to 2-mercaptobenzimidazole by comparing with an authentic sample of 2-mercaptobenzimidazole purchased from Aldrich Chemical Co.

EXAMPLE 39

Effects of compounds of Formula I on Gastric Acid Secretions in Rats

Fasted, adult (140–240 g), male, Sprague-Dawley rats were fasted for 24 h from food, but not water, and then treated by oral gavage with 1 to 1.5 mL total volume of compound of Formula I (300 μmmol/Kg) on different days. Two hours later, rats were anesthetized with a combination of pentobartital and thiopental, the abdomen was opened and the pylorus was ligated, and tracheal, gastric, and peripheral venous canulas were placed. The stomachs were lavaged with 10 mL 0.9% saline every 10 min. for 30 min and the gastric effluent collected in receptacles to determine the basal acid secretion. Acid output was determined in each gastric effluent sample by back-titration to pH 7.0 using 0.02M NaOH. Then, 5 mL of an 8% peptone meal (pH 5.5) was instilled into the stomachs, mixed, and drained after 10 min each time for 2 hours. Acid output was determined in each gastric effluent containing the peptone meal by back-titration to pH 5.5 using 0.02M NaOH.

In the controlled vehicle (n=6), 8% peptone stimulated acid output is noted at 160 mmol/30 min after 1 hr., while rats dosed with 7-methoxy-3-[(4-methoxy-3,5-dimethyl-2-pyridyl)oxomethyl]-1,2,4-thiadiazolo[4,5-a]benzimidazole have an observed level of acid output at 20 μmmol/30 min after 1 h. 7-Methoxy-3-[(4-methoxy-3,5-dimethyl-2-pyridyl)oxomethyl]-1,2,4-thiadiazolo[4,5-a]benzimidazole demonstrated significant (p<0.05) inhibition of meal-stimulated acid secretion at 300 μmol/kg doses.

EXAMPLE 40

Effects of compounds of Formula I on Gastric Acid Secretions in Rats (Dose-dependent study)

Fasted, adult (140–240 g), male, Sprague-Dawley rats were fasted for 24 h from food, but not water, and then treated by oral gavage with 1 to 1.5 mL total volume of 4 different doses (0.3, 3, 30, and 300 μmol/kg) of each compound on different days. Two hours later, rats were anesthetized with a combination of pentobartital and thiopental, the abdomen was opened and the pylorus was ligated, and tracheal, gastric, and peripheral venous canulas were placed. The stomachs were lavaged with 10 mL 0.9% saline every 10 min. for 30 min and the gastric effluent collected in receptacles. Acid output was determined in each gastric effluent sample by back-titration to pH 7.0 using 0.02M NaOH. Then, 5 mL of an 8% peptone meal (pH 5.5) was instilled into the stomachs, mixed, and drained after 10 min each time for 2 hours. Acid output was determined in each gastric effluent sample by back-titration to pH 7.0 using 0.02M NaOH. After measuring basal acid output for at least 30 minutes, acid output was then measured during a 2 h intravenous infusion of histamine (5 mg/kg).

FIG. 5 shows gastric acid output (mmol/min) after administration of vehicle and after administration of 4 doses of 7-methoxy-3-[(4-methoxy-3,5-dimethyl-2-pyridyl)oxomethyl]-1,2,4-thiadiazolo[4,5-a]benzimidazole (0.3, 3, 30, and 300 mmol/kg) in anesthetized rats.

7-methoxy-3-[(4-methoxy -3,5-dimethyl-2-pyridyl)oxomethyl]-1,2,4-thiadiazolo[4,5-a]benzimidazole demonstrated significant (p<0.05 ) inhibition of histamine-stimulated acid secretion at 3, 30, 300 μmol/kg doses.

EXAMPLE 41

In Vitro Inhibition of Gastric Acid Secretion By 3-(4-methyl-1-piperazinyl)-1,2,4-thiadiazolo[4,5-a]benzimidazole dihydrochloride Acid secretion is measured indirectly by the accumulation of the weak base $^{14}$C-aminopyrine in the isolated murine gastric glands of mouse. The assay is performed in polypropylene eppendorf tubes containing 0.5 mL of resuspended mouse gastric glands. In addition, tubes contain the tested drug, acid secretagogues (e.g. histamine, di-butyryl cyclic AMP (cAMP), carbachol) and aminopyrine. Tubes are incubated for 60 min. at 37° C. and continuously rotated. The reaction is stopped by centrifugation of the gland suspension for five min. at 1500 g. Supernatant is aspirated leaving the pellet containing intact gastric glands. The pellet is washed extensively and digested overnight in 1 mL of Protosol (Amersham). After neutralisation with acetic acid and addition of scintillation fluid, the radioactivity is counted in a beta-counter (Beckman). The amount of radioactivity trapped in the pellet corresponds directly with the amount of acid being secreted. Each experimental point is done in triplicate. In each experiment, energy independent consumption was estimated with 0.1 mM of dinitrophenol and basal acid secretion in the absence of acid stimulants. These values were then subtracted from corresponding results in order to calculate basal or secretagogue stimulated acid secretion.

Mouse glands respond to a variety of conventional secretagogues and post-receptor mediators but not to gastrin. The maximum stimulation of acid secretion is achieved with 1 mM cAMP, 0.1 mM histamine, 0.1 mM IBMX, 10 µM carbachol, 10 µM forskolin, 10 µM calcium ionophore A23187, 1 µM thapsigarin. Each experiment is repeated a number of times and all results are expressed as a % of the maximum stimulation. For the purpose of comparing the relative potency of the compounds, each experiment contains positive controls using omeprazole for post-receptor/cAMP mediated responses and ranitidine which inhibits histamine mediated acid secretion.

3-(4-Methyl-1-piperazinyl)-1,2,4-thiadiazolo[4,5-a]benzimidazole dihydrochloride completely inhibited cAMP and histamine stimulated acid secretion at 100 µM. Using the above procedure, the $ED_{50}$ value for this compound was found to be 50 µM.

What is claimed is:

1. Imidazo[1,2-d]-thiadiazole compounds corresponding to the general formula I:

(I)

wherein

X and Z are independently hydrogen, lower alkyl, halo, nitro, hydroxy, lower alkoxy, a group NR'R", OC(O)R', OC(O)OR', OC(O)NR'R", NR'(COR'), NHC(O)NR'R", or NHC(O)OR', with R' and R" being independently hydrogen, lower alkyl, aryl or lower arylalkyl, or R' and R" in NR'R" when taken together forming with the N-atom a five or six membered heterocyclic ring

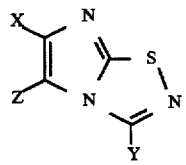

wherein n=4 or 5;

or X and Z taken together represent a benzene ring fused to the imidazo ring and being optionally substituted with up to four substituents independently selected from hydrogen, lower alkyl, halo, nitro, hydroxy, lower alkoxy, or a group NR'R", OC(O)R', OC(O)OR', OC(O)NR'R", NR'(COR'), NHC(O)NR'R", or NHC(O)OR', with R', R" being as defined above;

and Y is selected from:

(1) groups of the formula:

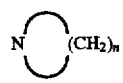

in which $R^7$ represents hydrogen, hydroxy, lower alkyl, lower cycloalkyl, lower alkoxy, lower alkenyl, lower alkynyl, aryl, lower arylalkyl, heterocyclyl, heterocyclyloxy, heterocyclyl-loweralkylene, groups NR'R" where R' and R" are as defined above, or groups ANR'R", AOR' wherein A is an amino acid residue or a peptide of 2 to 3 amino acid residues and R', R" are as defined above;

(2) heterocyclyl or lower alkylene-heterocyclyl, the heterocyclic ring being attached at any heteroatom or carbon atom which results in the creation of a stable structure, and the heterocyclic ring being optionally substituted with lower alkyl, lower acyl, lower alkoxycarbonyl, lower alkylsulfonyl or amido, with the proviso that the heterocyclyl is not 1-imidazolyl or substituted 1-imidazolyl;

(3) NR'R" wherein R', R" have the same definition as above;

(4) ANR'R", AOR' wherein A is an amino acid residue or a peptide of 2 to 3 amino acid residues and R', R" have the same definition as above;

(5) lower 2-(alkoxycarbonyl)alkyl;

(6) halo;

(7) groups of formula $R^8$—CHOH— wherein $R^8$ is hydrogen, lower alkyl, aryl, lower arylalkyl, lower cycloalkyl, lower alkenyl, lower alkynyl or heterocyclyl, the heterocyclic ring being attached at any heteroatom or carbon atom which results in the creation of a stable structure;

(8) groups of formula R'—(C=NOR$^{10}$)— wherein $R^{10}$ is hydrogen, lower alkyl or lower arylalkyl, and R' is lower alkyl, aryl, lower arylalkyl, lower cycloalkyl, lower alkenyl, lower alkynyl or heterocyclyl, the heterocyclic ring being attached at any carbon atom which results in the creation of a stable structure;

(9) lower alkoxy, lower arylalkoxy, lower cycloalkoxy, lower heterocyclyl alkoxy or heterocyclyloxy;

(10) lower alkylsulfonyl, lower alkylsulfinyl, arylsulfonyl, arylsulfinyl, lower arylalkylsulfonyl, lower arylalkylsulfinyl, heterocyclylsulfonyl, heterocyclylsulfinyl; optionally substituted with 1 to 2 substituents selected from lower alkyl, halo, nitro, hydroxy, lower alkoxy, or groups of formula NR'R", OC(O)R', OC(O)OR', OC(O)NR'R", NR'(COR'), NHC(O)NR'R", NHC(O)OR' where R' and R" are as defined above;

(11) groups of the formula —(C=NOH)COOR$^{11}$ wherein $R^{11}$ is lower alkyl

(12) hydrogen, aryl, lower arylalkyl, lower cycloalkyl, each group being optionally substituted with 1 to 2 substituents selected from halo, nitro, amino, hydroxy, lower alkoxy, lower alkylamino, lower dialkylamino, NR'R", OC(O)R', OC(O)OR', OC(O)NR'R", NR'(COR'), NHC(O)NR'R", NHC(O)OR', with R' and R" being as defined above.

2. Compounds according to claim 1, having the general formula:

[Structural formula: benzene ring with substituents R¹, R², R³, R⁴ fused to a thiadiazolo-benzimidazole system bearing group Y]

or pharmaceutically acceptable salts thereof, wherein R¹, R², R³, R⁴ are independently hydrogen, lower alkyl, halo, nitro, hydroxy, lower alkoxy, or groups of the formula NR'R", OC(O)R', OC(O)OR', OC(O)NR'R", NR'(COR'), NHC(O)NR'R", NHC(O)OR' in which R' and R" are as defined in claim 1, and Y is selected from:

(1) groups of the formula:

$$-\underset{\underset{R^7}{|}}{C}=O$$

in which $R^7$ represents hydrogen, hydroxy, lower alkyl, lower cycloalkyl, lower alkoxy, lower alkenyl, lower alkynyl, aryl, lower arylalkyl, heterocyclyl, heterocyclyloxy, heterocyclyl-loweralkylene, groups NR'R" where R' and R" are as defined in claim 1, or groups ANR'R", AOR' wherein A is an amino acid residue or a peptide of 2 to 3 amino acid residues and R', R" are as defined in claim 1;

(2) heterocyclyl or lower alkylene-heterocyclyl, the heterocyclic ring being attached at any heteroatom or carbon atom which results in the creation of a stable structure, and the heterocyclic ring being optionally substituted with lower alkyl, lower acyl, lower alkoxycarbonyl, lower alkylsulfonyl or amido, with the proviso that the heterocyclyl is not 1-imidazolyl or substituted 1-imidazolyl;

(3) NR'R" wherein R', R" have the same definition as above;

(4) ANR'R", AOR' wherein A is an amino acid residue or a peptide of 2 to 3 amino acid residues and R', R" have the same definition as above;

(5) lower 2-(alkoxycarbonyl)alkyl;

(6) halo;

(7) groups of formula $R^8$—CHOH— wherein $R^8$ is hydrogen, lower alkyl, aryl, lower arylalkyl, lower cycloalkyl, lower alkenyl, lower alkynyl or heterocyclyl, the heterocyclic ring being attached at any heteroatom or carbon atom which results in the creation of a stable structure;

(8) groups of formula $R^9$—C(=NOR¹⁰)— wherein $R^{10}$ is lower alkyl or lower arylalkyl, and $R^9$ is lower alkyl, aryl, lower arylalkyl, lower cycloalkyl, lower alkenyl, lower alkynyl or heterocyclyl, the heterocyclic ring being attached at any carbon atom which results in the creation of a stable structure;

(9) lower alkoxy, lower arylalkoxy, lower cycloalkoxy, lower heterocyclylalkoxy or heterocyclyloxy;

(10) lower alkylsulfonyl, lower alkylsulfinyl, arylsulfonyl, arylsulfinyl, lower arylalkylsulfonyl, lower arylalkylsulfinyl, heterocyclylsulfonyl, heterocyclylsulfinyl; optionally substituted with 1 to 2 substituents selected from lower alkyl, halo, nitro, hydroxy, lower alkoxy, or groups of formula NR'R", OC(O)R', OC(O)OR', OC(O)NR'R", NR'(COR'), NHC(O)NR'R", NHC(O)OR' where R' and R" are as defined in claim 1;

(11) groups of the formula —(C=NOH)COR¹¹ wherein $R^{11}$ is lower alkyl

(12) hydrogen, aryl, lower arylalkyl, lower cycloalkyl, each group being optionally substituted with 1 to 2 substituents selected from halo, nitro, amino, hydroxy, lower alkoxy, lower alkylamino, lower dialkylamino, NR'R", OC(O)R', OC(O)OR', OC(O)NR'R", NR'(COR'), NHC(O)NR'R", NHC(O)OR', with R' and R" being as defined in claim 1.

3. Compounds according to claim 2 wherein R¹, R², R³ and R⁴ each represents hydrogen or alkoxy.

4. Compounds according to claim 3 wherein R¹, R³ and R⁴ are each hydrogen and R² is either hydrogen or methoxy.

5. Compounds according to claim 4 in which Y is a group of formula:

$$-\underset{\underset{R^7}{|}}{C}=O$$

in which $R^7$ represents lower alkyl, lower arylalkyl, optionally substituted phenyl naphthyl, heterocyclyl, or hydroxy or lower alkoxy.

6. Compounds according to claim 5 wherein $R^7$ represents optionally substituted heterocyclyl.

7. Compounds according to claim 6 wherein $R^7$ represents 2-pyridyl either unsubstituted or substituted with 1 to 3 substituents selected from methyl and methoxy.

8. Compounds according to claim 7 wherein $R^7$ represents 3,5-dimethyl-4-methoxy-2-pyridyl.

9. A compound according to claim 8 which is 7-methoxy-3-[(4-methoxy-3,5-dimethyl-2-pyridyl)oxomethyl]-1,2,4-thiadiazolo[4,5-a]benzimidazole.

10. A compound according to claim 8 which is 3-[(4-methoxy-3,5-dimethyl-2-pyridyl)oxomethyl]-1,2,4-thiadiazolo[4,5-a]benzimidazole.

11. Compounds according to claim 5 wherein $R^7$ represents optionally substituted phenyl or naphthyl.

12. Compounds according to claim 11 wherein $R^7$ represents unsubstituted phenyl.

13. A compound according to claim 12 which is 3-(oxophenylmethyl)-1,2,4-thiadiazolo[4,5-a]benzimidazole.

14. Compounds according to claim 5 wherein $R^7$ represents hydroxy.

15. A compound according to claim 14 which is 3-carboxy-1,2,4-thiadiazolo[4,5-a]benzimidazole.

16. Compounds according to claim 4 wherein Y is an optionally substituted heterocyclic group bonded directly to the thiadiazolo ring.

17. Compounds according to claim 16 wherein the heterocyclic moiety of group Y is selected from unsubstituted pyridyl, piperazinyl, morpholinyl and pyrrolidinyl.

18. A compound according to claim 17 which is 3-(2-pyridyl)-1,2,4-thiadiazolo[4,5-a]benzimidazole.

19. A compound according to claim 17 which is 3-(4-methyl-1-piperazinyl)-1,2,4-thiadiazolo[4,5-a]benzimidazole.

20. A compound according to claim 17 which is 3-(4-morpholinyl)-1,2,4-thiadiazolo[4,5-a]-benzimidazole.

21. A compound according to claim 17 which is 3-(1-pyrrolidinyl)-1,2,4-thiadiazolo[4,5-a]-benzimidazole.

22. A compound according to claim 17 which is 3-(4-acetyl-1-piperazinyl)-1,2,4-thiadiazolo[4,5-a]benzimidazole.

23. Compounds according to claim 4 wherein Y is halo.

24. Compounds according to claim 23 wherein Y is bromo.

25. A compound according to claim 23 which is 3-bromo-1,2,4-thiadiazolo[4,5-a]benzimidazole.

26. A compound according to claim 4, which is 3-(4-methylphenylsulfonyl)-1,2,4-thiadiazolo[4,5-a]benzimidazole.

27. Compounds according to claim 1 having the general formula III:

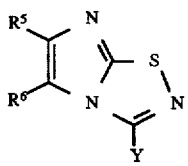

and pharmaceutically acceptable salts thereof, wherein $R^5$ and $R^6$ are independently selected from the group which are independently hydrogen, lower alkyl, halo, nitro, hydroxy, lower alkoxy, or groups of the formula NR'R", OC(O)R', OC(O)OR', OC(O)NR'R", NR'(COR'), NHC(O)NR'R", NHC(O)OR' in which R' and R" are as defined in claim 1; and Y is selected from:

(1) groups of the formula:

in which $R^7$ represents hydrogen, hydroxy, lower alkyl, lower cycloalkyl, lower alkoxy, lower alkenyl, lower alkynyl, aryl, lower arylalkyl, heterocyclyl, hetero-cyclyloxy, heterocyclyl-lower alkylene, groups NR'R" where R' and R" are as defined in claim 1, or groups ANR'R", AOR' wherein A is an amino acid residue or a peptide of 2 to 3 amino acid residues and R', R" are as defined in claim 1;

(2) heterocyclyl or lower alkylene-heterocyclyl, the heterocyclic ring being attached at any heteroatom or carbon atom which results in the creation of a stable structure, and the heterocyclic ring being optionally substituted with lower alkyl, lower acyl, lower alkoxycarbonyl, lower alkylsulfonyl or amido, with the proviso that the heterocyclyl is not 1-imidazolyl or substituted 1-imidazolyl;

(3) NR'R" wherein R', R" have the same definition as above;

(4) ANR'R", AOR' wherein A is an amino acid residue or a peptide of 2 to 3 amino acid residues and R', R" are as defined in claim 1;

(5) lower 2-(alkoxycarbonyl)alkyl;

(6) halo;

(7) groups of formula $R^8$—CHOH— wherein $R^8$ is hydrogen, lower alkyl, aryl, lower arylalkyl, lower cycloalkyl, lower alkenyl, lower alkynyl or heterocyclyl, the heterocyclic ring being attached at any heteroatom or carbon atom which results in the creation of a stable structure;

(8) groups of formula $R^9$—C(=$NOR^{10}$)— wherein $R^{10}$ is hydrogen, lower alkyl or lower arylalkylyl, and R' is lower alkyl, aryl, lower arylalkyl, lower cycloalkyl, lower alkenyl, lower alkynyl or heterocyclyl, the heterocyclic ring being attached at any carbon atom which results in the creation of a stable structure;

(9) lower alkoxy, lower arylalkoxy, lower cycloalkoxy, lower heterocyclylalkoxy, or heterocyclyoxy;

(10) lower alkylsulfonyl, lower alkylsulfinyl, arylsulfonyl, arylsulfinyl, lower arylalkylsulfonyl, lower arylalkylsulfinyl, heterocyclylsulfonyl, heterocyclylsulfinyl; optionally substituted with 1 to 2 substituents selected from lower alkyl, halo, nitro, hydroxy, lower alkoxy, or groups of formula NR' R", OC(O)R', OC(O)OR', OC(O)NR'R", NR'(COR'), NHC(O)NR'R", NHC(O)OR' where R' and R" are as defined in claim 1;

(11) groups of the formula —C=NOH—$COOR^{11}$ wherein $R^{11}$ is lower alkyl;

(12) aryl, lower arylalkyl, lower cycloalkyl, each group being optionally substituted with 1 to 2 substituents selected from halo, nitro, amino, hydroxy, lower alkoxy, lower alkylamino, lower dialkylamino, NR'R", OC(O)R', OC(O)OR', OC(O)NR'R", NR' (COR'), NHC(O)NR'R", NHC(O)OR', with R' and R" being as defined in claim 1.

28. Compounds according to claim 27 wherein $R^5$ and $R^6$ both represent hydrogen.

29. Compounds according to claim 28 wherein Y represents

and $R^7$ represents lower alkyl, lower alkoxy or aryl.

30. A compound according to claim 29 which is 3-acetylimidazo[1,2-d]-1,2,4-thiadiazole.

31. A compound according to claim 29 which is 3-benzoylimidazo[1,2-d]-1,2,4-thiadiazole.

32. Pharmaceutical compositions for use in treating peptic ulcers in animals, comprising an effective dosage amount of an active ingredient of a compound of formula I as defined in claim 1, in association with a pharmaceutically acceptable carrier.

* * * * *